(12) United States Patent
Scheurich

(10) Patent No.: US 8,906,351 B2
(45) Date of Patent: Dec. 9, 2014

(54) 2,2'-FUROIN DERIVATIVES AND USE THEREOF TO LIGHT SKIN

(75) Inventor: Rene Peter Scheurich, Gross-Zimmern (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/817,854

(22) PCT Filed: Aug. 18, 2011

(86) PCT No.: PCT/EP2011/004160
§ 371 (c)(1),
(2), (4) Date: Feb. 20, 2013

(87) PCT Pub. No.: WO2012/034629
PCT Pub. Date: Mar. 22, 2012

(65) Prior Publication Data
US 2013/0164230 A1    Jun. 27, 2013

(30) Foreign Application Priority Data
Sep. 17, 2010 (DE) .......................... 10 2010 045 890

(51) Int. Cl.
*C07D 407/06* (2006.01)
*A61Q 17/04* (2006.01)
*A61Q 19/02* (2006.01)
*A61K 8/49* (2006.01)

(52) U.S. Cl.
CPC .............. *A61Q 19/02* (2013.01); *C07D 407/06* (2013.01); *A61Q 17/04* (2013.01); *A61K 8/4973* (2013.01)
USPC ................................ 424/59; 424/62; 549/473

(58) Field of Classification Search
None
See application file for complete search history.

(56) References Cited

U.S. PATENT DOCUMENTS

| 5,364,617 | A  | * | 11/1994 | Bush et al. ....................... 424/59 |
| 8,278,288 | B2 |   | 10/2012 | Ferritto et al. |
| 2004/0214192 | A1 | * | 10/2004 | Hashida et al. ................... 435/6 |
| 2005/0255055 | A1 | * | 11/2005 | Wagner et al. .................. 424/59 |
| 2010/0221201 | A1 |   | 9/2010 | Ferritto et al. |
| 2013/0004445 | A1 |   | 1/2013 | Ferritto et al. |

FOREIGN PATENT DOCUMENTS

WO    WO-2009 045709    4/2009

OTHER PUBLICATIONS

International Search Report for PCT/EP2011/004160, Date of completion of the international search: Oct. 6, 2011, Date of mailing of the international search report: Oct. 13, 2011.

* cited by examiner

*Primary Examiner* — Robert A Wax
*Assistant Examiner* — Randeep Singh
(74) *Attorney, Agent, or Firm* — Millen, White, Zelano & Branigan, P.C.

(57) ABSTRACT

The invention relates to the use of compounds of the formula (I), in which R1, R2, m and n have the meanings indicated in the Claims, and/or physiologically acceptable salts, tautomers, stereoisomers and/or solvates thereof, including mixtures thereof in all ratios, for the inhibition of tyrosinase and for lightening the skin. The invention also relates to the use of the compounds of the formula (I) in the prophylaxis, therapy or progress control of pigment disorders of the skin. The invention furthermore relates to preparations comprising the compounds of the formula (I) in combination with at least one further active compound and to a process for the preparation of the preparations by mixing the compounds of the formula (I) with a vehicle which is physiologically acceptable for topical applications.

22 Claims, No Drawings

2,2'-FUROIN DERIVATIVES AND USE THEREOF TO LIGHT SKIN

The invention relates to the use of compounds of the formula (I)

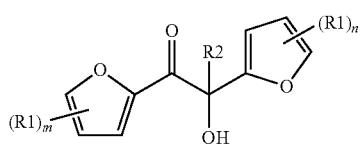

in which R1, R2, m and n have the meanings indicated in the Claims, and/or physiologically acceptable salts, tautomers, stereoisomers and/or solvates thereof, including mixtures thereof in all ratios, for the inhibition of tyrosinase and for lightening the skin. The invention also relates to the use of the compounds of the formula (I) in the prophylaxis, therapy or progress control of pigment disorders of the skin. The invention furthermore relates to preparations comprising the compounds of the formula (I) in combination with at least one further active compound and to a process for the preparation of the preparations by mixing the compounds of the formula (I) with a vehicle which is physiologically acceptable for topical applications.

Skin and hair colour are dependent on the content, size and type of the nitrogen-containing, dark dye melanin, which is produced in the cells which are capable of melanin formation (melanocytes). Starting from tyrosine and with the aid of various melanocyte-specific enzymes, such as, for example, tyrosinase or tyrosinase-related proteins, melanin is synthesised within the melanocytes. The melanin is subsequently transferred to the keratinocytes in the form of so-called melanosomes. Although the melanin in the skin is suitable protection against UV radiation, darker or overpigmented skin may affect beauty and result in serious aesthetic problems. Hyperpigmented skin areas or lesions contain melasma (also known as chloasma), i.e. yellowish-brown spots of irregular shape.

In the case of pigment spots, a distinction is generally made between freckles (ephelides), age spots (lentigines), so-called age warts (verrucae seborrhoica) and hyperpigmentation (for example chloasma or melasma). People with very pale skin and reddish hair, in particular, tend towards freckles. By contrast, hyperpigmentation (chloasma) is frequently found in women who regularly introduce oestrogens into their body. The sun very frequently plays an important role. Prevention can be achieved, in particular, by regular sun protection with a high light protection factor. In order to remove unattractive pigment spots, various possibilities are available, such as lasers, dermabrasion or other electrosurgical methods and so-called bleaching creams. The latter alternative has the advantage that it is significantly less expensive for the patient than the electrosurgical methods. In addition, application is simpler and more pleasant.

A large number of compounds having a skin-lightening action is available on the market for the treatment of pigment spots. These are, inter alia, compounds such as, for example, kojic acid, arbutin, aloesin, niacinamide, vitamin C or rucinol, which suppress melanin production in the skin. This can take place utilising various mechanisms. However, skin-lightening substances usually delay the conversion of tyrosine into melanin by blocking the enzyme tyrosinase. However, these compounds have a number of disadvantages, such as, for example, low depigmentation efficiency, side effects, such as skin irritation or skin exfoliation (skin peeling), cell damage, low penetration through the skin or short shelf life or low stability of the formulations. There is therefore a need for novel safe skin lighteners having higher effectiveness and good formulation properties.

The invention is based on the object of overcoming the disadvantages indicated in the prior art and developing effective compounds which have effective capability for skin lightening—with the aim of improving the cosmetic or therapeutic efficacy at the same time as reducing the side effects.

The object of the invention is achieved in accordance with the independent claims. The sub-claims contain preferred embodiments. In accordance with the invention, the compounds of the formula (I)

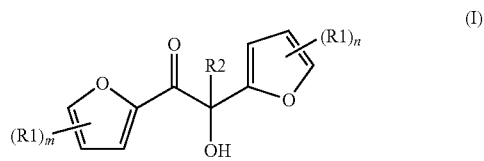

in which
R1 denotes A, Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar,
R2 denotes H, A, Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar,
Y denotes H or Alk,
A denotes unbranched or branched alkyl having 1-18 C atoms, where, independently of one another, 1-3H atoms may be replaced by F and/or, independently of one another, one or two adjacent CH$_2$ groups may be replaced by —O—, —N(Alk)-, a —CH=CH— and/or —C≡C— group,
Alk denotes unbranched or branched alkyl having 1-12 C atoms,
Cyc denotes cyclic alkyl having 3-10 C atoms, where, independently of one another, 1-3H atoms may be replaced by F and/or, independently of one another, one or two adjacent CH$_2$ groups may be replaced by —O—, —N(Alk)-, a —CH=CH— and/or —C≡C— group,
Ar denotes a mono-, bi- or tricyclic aromatic carbocycle having 3 to 20 C atoms, which may be unsubstituted or mono-, di- or trisubstituted by F, A, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY, and
m, n, p, independently of one another, denote 0, 1, 2 or 3,
and/or physiologically acceptable salts, tautomers, stereoisomers and/or solvates thereof, including mixtures thereof in all ratios,
are used for lightening the skin. For the purposes of the invention, lightening the skin is preferably taken to represent a non-therapeutic use.

Likewise in accordance with the invention, the compounds of the formula (I), as described above, and/or physiologically acceptable salts, tautomers, stereoisomers and/or solvates thereof, including mixtures thereof in all ratios, are used for the inhibition of tyrosinase.

In a further embodiment of the invention, the compounds of the formula (I), as described above, and/or physiologically acceptable salts, tautomers, stereoisomers and/or solvates thereof, including mixtures thereof in all ratios, are used for the prophylaxis, therapy and/or progress control of pigment disorders of the skin.

Surprisingly, it has been found that the compounds of the formula (I) have been provided with tyrosinase-inhibiting properties. The compounds of the formula (I) and in particular of the part-formulae (IA), (IB) and (IC) are, due to their core structure of 2,2'-furoin, to which the substituents R1 and R2 are attached, structured in such a way that a potent and selective inhibition of tyrosinase occurs. The use of the compounds having the formula (I) thus opens up completely new possibilities with respect to the skin-lightening action. Remarkably, the compounds of the formula (I) play a role in the treatment of pigment spots of all types by suppressing the synthesis of melanin and preventing melanin overproduction. The role of the compounds of the formula (I) here can be of both a non-therapeutic and therapeutic nature.

It was hitherto merely known from WO 1996/09807 that 2-hydroxy-1-ethanone derivatives are suitable for the colouring of keratin-containing fibres, such as, for example, human hair. The derivatives address colourings in the orange, brown, red-brown, blue-black and black region, in particular on joint administration with compounds containing primary and secondary amino group, nitrogen-containing heterocycles or aromatic hydroxyl compounds. By contrast, the present invention reveals that precisely through the use of the compounds of the formula (I) and/or physiologically acceptable salts, tautomers, stereoisomers and/or solvates thereof, including mixtures thereof in all ratios, the skin is lightened in an excellent manner, especially the human skin. Preference is given for the purposes of the invention to the use of at least one compound of the formula (I), as described herein, including embodiments, for the cosmetic lightening of the skin, particularly preferably for the cosmetic lightening of the human skin. To this extent, pigment spots can be treated cosmetically, i.e. non-therapeutically, where the pigment spots encompass, in particular, hyperpigmentation, freckles, age spots and/or sun spots. Likewise in accordance with the invention, the compounds of the formula (I) described can be used cosmetically, in particular, in the case of skin ageing, as can be caused, for example, by environmental factors.

The compounds of the formula (I) and salts thereof consequently simultaneously have valuable cosmetic and/or pharmacological properties while being well tolerated in that the lightening of the skin is accompanied by a relative melanin content of less than 90%, preferably less than 80%, particularly preferably less than 70%.

In particular, the compounds of the formula (I) described are tyrosinase inhibitors and, owing to this property, exhibit the desired activity as skin lightener. The invention thus relates to the use of at least one compound of the formula (I) or part-formulae thereof and/or physiologically acceptable salts, tautomers, stereoisomers and/or solvates thereof, including mixtures thereof in all ratios, for the inhibition of tyrosinase, preferably also in vitro. The term "inhibition" relates to any reduction in the activity which is based on the action of the specific compounds according to the invention in that the latter are capable of interacting with the target molecule in such a way that recognition, bonding and blocking is facilitated. The compounds are distinguished by high affinity to tyrosinase, ensuring reliable bonding and preferably complete blocking of the oxidase activity. The compounds are particularly preferably monospecific in order to guarantee exclusive and direct recognition of the selected oxidase. The term "recognition" here relates to any type of interaction between the compound and the target molecules mentioned, in particular covalent or non-covalent bonding, such as, for example, covalent bonding, hydrophobic/hydrophilic interactions, van der Waals forces, ion attraction, hydrogen bonds or ligand-receptor interactions.

The use of the compounds of the formula (I) exhibits an advantageous biological activity which is detectable in the tests described herein, such as, for example, enzyme-based assays. The measurement of the oxidase activity is a technique which is well known to the person skilled in the art.

The above-mentioned use of the compounds can take place in in-vitro or in-vivo models. The susceptibility of a particular cell to treatment with the compounds of the formula (I) can be determined by testing in vitro. Typically, a culture of the cell is incubated with a compound according to the invention at various concentrations for a period of time which is sufficient to enable the active agents to inhibit the synthesis of melanin, usually between approximately one hour and one week. For testing in vitro, cultivated cells from a biopsy sample can be used. The amount of melanin remaining in the cells after the treatment is then determined. The use in vitro takes place, in particular, on samples of mammal species which are suffering from pigment disorders of the skin. The host or patient can belong to any mammal species, for example a primate species, in particular humans, but also rodents (including mice, rats and hamsters), rabbits, horses, cows, dogs, cats, etc. Animal models are of interest for experimental investigations, providing a model for the treatment of a human disease or cosmetic anomaly.

The testing of a plurality of specific compounds enables the selection of the active compound which appears the most suitable for the treatment of the patient. The in-vivo dose of the selected compound is advantageously matched to the susceptibility of tyrosinase and/or severity of the pigment disorder of the patient taking into account the in-vitro data, as a result of which the therapeutic efficacy is noticeably increased. The dose varies depending on the specific compound used, the specific disease, the patient status, etc. A cosmetic dose is typically sufficient considerably to reduce the undesired amount of melanin in the target tissue, while the quality of life of the patient is maintained and ultimately improved. The following teaching of the invention and embodiments thereof relating to the use of compounds of the formula (I) for prophylaxis, therapy and/or progress control is valid and can be applied without restrictions to the use of the compounds for the inhibition of tyrosinase activity, if it appears appropriate.

The use is generally continued until a considerable reduction in the tyrosinase activity and melanin production has occurred, for example at least about 10% reduction of the melanin content, and can be continued until essentially no further undesired overproduction of melanin in the body is detected. It goes without saying here that skin lightening represents a repeated or ongoing treatment, since, after removal of the preparations of the formula (I), the normal melanin synthesis rate is taken up again. In tests of this type, the compounds according to the invention exhibit and cause an inhibiting effect, which is usually documented by $IC_{50}$ values in a suitable range, preferably in the micromolar range and more preferably in the nanomolar range. Tyrosinase is, in particular, inhibited to the extent of 50% if the concentration of the compounds is less than 1 µM, preferably less than 0.5 µM, particularly preferably less than 0.1 µM. This concentration is called the $IC_{50}$ value.

In accordance with the invention, compounds of the formula (I) and/or physiologically acceptable salts, tautomers, stereoisomers and/or solvates thereof, including mixtures thereof in all ratios, are suitable for use in the prophylaxis, therapy and/or progress control of diseases which are caused, promoted and/or spread by tyrosinase activity. The use of the compounds of the formula (I) or part-formulae thereof and/or physiologically acceptable salts, tautomers, stereoisomers and/or solvates thereof, including mixtures thereof in all ratios, for the prophylaxis, therapy and/or progress control of diseases which are caused, promoted and/or spread by tyrosinase activity is also in accordance with the invention. The present invention therefore also relates to the use of compounds of the formula (I) or part-formulae thereof and/or physiologically acceptable salts, tautomers, stereoisomers and/or solvates thereof, including mixtures thereof in all ratios, for the preparation of a medicament for the prophylaxis, therapy and/or progress control of diseases which are caused, promoted and/or spread by tyrosinase activity. For the identification of a corresponding signalling pathway and in order to detect interactions between various signalling pathways, suitable models or model systems have been developed, for example cell-culture models (Khwaja et al. (1997) EMBO 16: 2783) and transgenic animal models (White et al. (2001) Oncogene 20: 7064). In order to determine certain stages in the signalling cascade, interacting compounds can be used in order to modulate the signal (Stephens et al. (2000) Biochemical J 351: 95). In addition, the compounds according to the invention can also be used as reagents for testing oxidase-dependent signalling pathways in animals and/or cell-culture models or in the clinical diseases mentioned in this application. As discussed herein, these signalling pathways are relevant for various diseases. Accordingly, the compounds according to the invention are useful in the prophylaxis, therapy and/or progress control of diseases which are dependent on signalling pathways with participation by tyrosinase.

In accordance with the invention, compounds of the formula (I) or part-formulae thereof and/or physiologically acceptable salts, tautomers, stereoisomers and/or solvates thereof, including mixtures thereof in all ratios, are suitable for use in the prophylaxis, therapy and/or progress control of pigment disorders selected from the group of hyperpigmentation, freckles, age spots and sun spots.

A further embodiment of the present invention relates to the use of the compounds of the formula (I) and/or physiologically acceptable salts, tautomers, stereoisomers and/or solvates thereof, including mixtures thereof in all ratios, in combination with at least one further active compound, which is preferably selected from the group of antioxidants, vitamins, UV filters, skin-lightening active compounds, self-tanning substances, anti-inflammatory agents, antimicrobial active compounds, active compounds which improve the skin moisture content, ageing-inhibiting active compounds (anti-ageing active compounds) and anticellulite active compounds.

For the purposes of the invention, the compounds of the formula (I) are defined in such a way that they are also taken to mean pharmaceutically or cosmetically usable derivatives, salts, hydrates, solvates, precursors of the compounds, tautomers and optically active forms (such as, for example, stereoisomers, diastereomers, enantiomers, racemates). Solvates of the compounds are taken to mean adductions of inert solvent molecules onto the compounds, which form owing to their mutual attractive force. Solvates are, for example, mono- or dihydrates or alcoholates. Pharmaceutically or cosmetically usable derivatives are taken to mean, for example, the salts of the compounds according to the invention and so-called precursors of the compounds. Precursors are taken to mean, for example, compounds of the formula (I) modified by means of alkyl or acyl groups, sugars or oligopeptides, which are rapidly cleaved in the organism to give the effective compounds according to the invention. These also include biodegradable polymer derivatives of the compounds according to the invention, as described, for example, in Int. J. Pharm. 115, 61-67 (1995). Any compound which can be converted in vivo into a bioactive agent, i.e. compounds of the formula (I), is a precursor in the sense of this invention. Any biologically active compound which results from the in-vivo metabolisation of a compound according to the invention is a metabolite in the sense of the present invention. The compounds of the formula (I) can have one or more chiral centres and therefore occur in various stereoisomeric forms. The formula (I) encompasses all these forms.

The invention also relates to the use of mixtures of the compounds of the formula (I), for example mixtures of two diastereomers, for example in the ratio 1:1, 1:2, 1:3, 1:4, 1:5, 1:10, 1:100 or 1:1000. Particular preference is given here to mixtures of stereoisomeric compounds.

Above and below, the radicals R1, R2, Y, A, alk, Cyc and Ar and the indices m, n and p have the meanings indicated for the formula (I), unless expressly indicated otherwise. If individual radicals occur multiple times within a compound or radical, the radicals adopt, independently of one another, the meanings indicated, unless expressly indicated otherwise. For example, the radicals YY in the radical R1, in which they occur multiple times, are identical or different, but are preferably in each case selected, independently of one another, from the meanings indicated above and/or below (for example methyl and/or ethyl), unless expressly indicated otherwise. It likewise goes without saying, for example, that the index m in the notation $(R1)_m$ indicates the frequency of the substitution by the radical R1, i.e. the furanyl radical may carry up to 3 radicals R1 in different positions (but not a concatenation of up to 3 radicals in the same position), where the respective radicals R1 are selected, identically or differently, but preferably in each case independently of one another, from the meanings indicated above and/or below. In addition, the radicals R1 in the formula (I) in which they occur generically twice are selected, identically or differently, but preferably in each case independently of one another, from the meanings indicated above and/or below (for example A and/or F). If R1 occurs multiple times, the radical may alternatively also be denoted by R1', R1", R1''', R1'''', R''''' and R''''''. The terms used here for the definition of the compounds are generally based on the rules of the IUPAC organisation for chemical compounds and in particular organic compounds. The terms for explanation of the above-mentioned compounds of the invention always have the following meanings, unless indicated otherwise in the description or claims.

The term "unsubstituted" means that a radical, a group or a residue carries no substituents. The term "substituted" means that a radical, a group or a residue carries one or more substituents.

"Alkyl" or "A" in the sense of the invention denotes a saturated or unsaturated hydrocarbon radical, which is unbranched (linear) or branched and preferably has 1, 2, 3, 4, 5, 6, 7, 8, 9, 10, 11, 12, 13, 14, 15, 16, 17 or 18 C atoms, i.e. $C_{1-18}$-alkanyl, $C_{2-18}$-alkenyls and $C_{2-18}$-alkynyls. Examples of alkyl radicals are methyl, ethyl, propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, pentyl, isopentyl, neopentyl, tertpentyl, 1-, 2-, 3- or 4-methylpentyl, hexyl, dodecyl. Furthermore, radicals which are derived from oleic, plamitic or stearic acid are usual, in particular in cosmetics, since they significantly increase the lipophilicity and pharmaceutical formulation and rheological properties can thus be controlled. Alkenyls have at least one C—C double bond and alkynyls have at least one C—C triple bond. Alkynyls may in addition have at least one C—C double bond. Examples of suitable alkenyls are allyl, vinyl, propenyl (—CH$_2$CH=CH$_2$; —CH=CH—CH$_3$; —C(=CH$_2$)—CH$_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl. Examples of suitable alkynyls are ethynyl, propynyl (—CH$_2$—C≡CH; —C≡C—CH$_3$), 1-, 2- or 3-butynyl, pentynyl, hexynyl or pent-3-en-1-ynyl, in particular propynyl. Radicals which in which a plurality of CH$_2$ groups may have been replaced by —CH=CH— and —C≡C— are also part of the present invention. Enyne compounds are readily accessible synthetically and can be transformed further in nature, for example by Bergmann cyclisation with building-up of additional ring systems.

In a preferred embodiment of the invention, "A" is unbranched or branched alkyl having 1, 2, 3, 4, 5, 6, 7, 8, 9, 10, 11, 12, 13, 14, 15, 16, 17 or 18 C atoms, where, independently of one another, 1, 2 or 3H atoms may be replaced by F and/or, independently of one another, one or two adjacent CH$_2$ groups may be replaced by —O—, —N(Alk)-, a —CH=CH— and/or —C≡C— group. "A" is particularly preferably unbranched or branched alkyl having 1, 2, 3, 4, 5, 6, 7 or 8 C atoms, where, independently of one another, 1, 2 or 3H atoms may be replaced by F and/or, independently of one another, one or two adjacent CH$_2$ groups may be replaced by —O—, —N(Alk)-, a —CH=CH— and/or —C≡C— group. Particularly preferred examples of the substituted "A" are hydroxyethyl, hydroxypropyl, alkoxyethyl (for example methoxyethyl, ethoxyethyl) and alkoxypropyl (for example methoxypropyl, ethoxypropyl). "A" very particularly preferably corresponds to the meaning "Alk". It goes without saying that the respective meanings of "A" are independent of one another in the radicals of a formula according to the invention.

The term "Alk" in the sense of the invention denotes unbranched or branched alkyl having 1, 2, 3, 4, 5, 6, 7, 8, 9, 10, 11 or 12 C atoms, where, independently of one another, 1, 2 or 3 H atoms may be replaced by F, preferably $C_{1-12}$-alkyl, particularly preferably $C_{1-4}$-alkyl. A $C_{1-4}$-alkyl of this type is very particularly preferably methyl, ethyl, propyl, isopropyl, butyl, isobutyl, sec-butyl, tert-butyl, fluoromethyl, difluoromethyl, trifluoromethyl or 1,1,1-trifluoro-ethyl, most preferably methyl, ethyl or trifluoromethyl. It goes without saying that the respective meanings of "Alk" are independent of one another in the radicals of a formula according to the invention.

"Cycloalkyl" or "Cyc" in the sense of the invention denotes saturated and partially unsaturated non-aromatic cyclic hydrocarbon groups having 1 to 3 rings which encompass 3 to 20, preferably 3 to 12, particularly preferably 3 to 10 C atoms. The bonding to the skeleton of the formula (I) can take place via any ring member of the cycloalkyl group. Examples of a suitable cycloalkyl are cyclopropyl, cyclobutyl, cyclopentyl, cyclohexyl, cycloheptyl, cyclooctyl, cyclodecyl, cyclopentenyl, cyclopentadienyl, cyclohexenyl and cyclooctadienyl and adamantyl, bicyclo[5.3.0]decapentaenyl (azulene radical), 1,7,7-trimethylbicyclo[2.2.1]-heptan-2-one (camphor radical) or 1-methyl-4-prop-1-en-2-ylcyclohexenyl (limonene radical).

In a preferred embodiment of the invention, "Cyc" is cyclic alkyl having 3, 4, 5, 6, 7, 8, 9 or 10 C atoms, where, independently of one another, 1, 2 or 3H atoms may be replaced by F and/or, independently of one another, one or two adjacent CH$_2$ groups may be replaced by —O—, —N(Alk)-, a —CH=CH— and/or —C≡C— group. Particular preference is given to cyclic alkyl having 3, 4, 5, 6, 7 or 8 C atoms, where, independently of one another, 1, 2 or 3H atoms may be replaced by F and/or, independently of one another, one or two adjacent CH$_2$ groups may be replaced by —O—, —N(Alk)- or a —CH=CH— group. Very particularly preferred examples thereof are cyclopropenyl, cyclobutenyl, cyclopentenyl, cyclopentadienyl, cyclohexenyl, cyclohexadienyl, cyclooctadienyl or norbornyl.

Skeleton of the formula (I) is any generic or non-generic structure to which any radical in the sense of the invention, such as, for example, Cyc or Ar, can be bonded in order to obtain a compound of the formula (I).

The term "aryl", "carboaryl" or "Ar" in the sense of the invention denotes a mono- or polycyclic aromatic hydrocarbon system having 3, 4, 5, 6, 7, 8, 9, 10, 11, 12, 13, 14, 15, 16, 17, 18, 19 or 20, preferably 5-14, particularly preferably 5-10, C atoms, which may optionally be substituted. The term "aryl" includes systems in which the aromatic ring is part of a bi- or polycyclic saturated, partially unsaturated and/or aromatic system, for example if the aromatic ring is fused to "aryl", "heteroaryl" or "heterocyclyl" via any desired ring member of the aryl radical. The bonding to the skeleton of the formula (I) can take place via any ring member of the aryl group. Examples of suitable "aryl" are phenyl, biphenyl, naphthyl, 1-naphthyl, 2-naphthyl, binaphthyl, anthracenyl, phenanthrenyl, indanyl, indenyl, 1,2,3,4-tetrahydronaphthyl, in particular phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-hydroxyphenyl, o-, m- or p-hydroxytolyl (cresol-like radicals), o-, m- or p-methoxyphenyl, o-, m- or p-aminophenyl, o-, m- or p-methylaminophenyl, o-, m- or p-dimethylaminophenyl, o-, m- or p-aminocarbonyl-phenyl, o-, m- or p-carboxyphenyl, o-, m- or p-methoxycarbonylphenyl, o-, m- or p-ethoxycarbonylphenyl, o-, m- or p-acetylphenyl.

In a preferred embodiment of the invention, "Ar" is a mono-, bi- or tricyclic aromatic carbocycle having 3 to 20 C atoms, which may be unsubstituted or mono-, di- or trisubstituted by F, A, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY. It is particularly preferred for "Ar" to denote mono-, bi- or tricyclic aryl having 5 to 14 C atoms, which may be unsubstituted or mono-, di- or trisubstituted by F, Alk or —(CY$_2$)$_p$—OY. Very particularly preferred examples are phenyl, naphthyl, anthracenyl or phenanthrenyl, which may be unsubstituted or mono- or disubstituted by F, Alk or —OAlk. It goes without saying that the respective meanings of "Ar" are independent of one another in the radicals of a formula according to the invention.

The radical R1 preferably denotes A, Cyc, F, OY or Ar, particularly preferably A, Cyc, F, OH or Ar.

The radical R2 preferably denotes H, A, Cyc, F, OY or Ar, particularly preferably H, Alk, Cyc, F, OH or Ar, very particularly preferably H.

The indices m, n and p preferably denote, independently of one another, 0, 1 or 2, particularly preferably, independently of one another, 0 or 1, very particularly preferably, independently of one another, 0, most preferably, dependent on one another, one of the above-mentioned meanings.

Accordingly, the invention relates to the compounds of the formula (I) for the use according to the invention in which at least one of the said radicals has one of the meanings indicated above. Radicals not denoted in greater detail in the context of an embodiment of the formula (I), part-formula thereof or any radical thereon are intended to have the meaning indicated for the formula (I), as disclosed herein, in order to achieve the object of the invention. This means that the said radicals may adopt all meanings assigned to them, as described above or below, including any preferred embodiments, without being restricted thereto and irrespective of their occurrence in another particular context. In particular, it goes without saying that any embodiment of a particular radical can be combined with any embodiment of one or more other radicals.

In a preferred embodiment of the present invention, 2,2'-furoin derivatives of the formula (I) and/or physiologically acceptable salts, tautomers, stereoisomers and/or solvates thereof, including mixtures thereof in all ratios, are provided for the use according to the invention, in which R1 denotes A, Cyc, F, OY or Ar,
R2 denotes Y, Cyc, F, OH or Ar,
Y denotes H or Alk,
A denotes unbranched or branched alkyl having 1-18 C atoms, where, independently of one another, 1-3H atoms may be replaced by F and/or, independently of one another, one or two adjacent $CH_2$ groups may be replaced by —O—, —N(Alk)-, a —CH=CH— or —C≡C— group,
Alk denotes unbranched or branched alkyl having 1-12 C atoms,
Cyc denotes cyclic alkyl having 3-8 C atoms, where, independently of one another, 1-3H atoms may be replaced by F and/or, independently of one another, one or two adjacent $CH_2$ groups may be replaced by —O—, —N(Alk)- or a —CH=CH—group,
Ar denotes mono-, bi- or tricyclic aryl having 5 to 14 C atoms, which may be unsubstituted or mono-, di- or trisubstituted by F, Alk or —$(CY_2)_p$—OY, and
m, n, p, independently of one another, denote 0, 1 or 2.

In a particularly preferred embodiment of the present invention, 2,2'-furoin derivatives of the formula (I) and/or physiologically acceptable salts, tautomers, stereoisomers and/or solvates thereof, including mixtures thereof in all ratios, are provided for the use according to the invention, in which R1 denotes A, Cyc, F, OH or Ar,
R2 denotes H,
Y, A, independently of one another, denote Alk,
Alk denotes methyl, ethyl or trifluoromethyl,
Cyc denotes cyloprenyl, cyclobutenyl, cyclopentenyl, cyclopentadienyl, cyclohexenyl, cyclohexadienyl or cyclooctadienyl,
Ar denotes phenyl, naphthyl, anthracenyl or phenanthrenyl, which may be unsubstituted or mono- or disubstituted by F, Alk or —$(CY_2)_p$—OY, and
m, n, p, independently of one another, denote 0 or 1.

In a very particularly preferred embodiment of the present invention, 2,2'-furoin of the part-formula (IA)

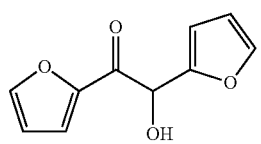

(IA)

and/or physiologically acceptable salts, tautomers, stereoisomers and/or solvates thereof, including mixtures thereof in all ratios, and/or 1,2-di-2-furanyl-2-hydroxy-2-phenylethanone of the part-formula (IB)

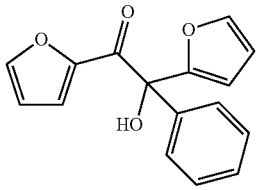

(IB)

and/or physiologically acceptable salts, tautomers, stereoisomers and/or solvates thereof, including mixtures thereof in all ratios,
are used in accordance with the invention.

Most preference is given to the use according to the invention of 2,2'-furoin of the part-formula (IA), i.e. use thereof for lightening the skin, for the inhibition of tyrosinase and/or in the prophylaxis, therapy and/or progress control of pigment disorders of the skin.

The compounds of the formula (I) and also the starting materials for their preparation are prepared by methods known per se, as are described in the literature (for example in standard works, such as Houben-Weyl, Methoden der organischen Chemie [Methods of Organic Chemistry], Georg-Thieme-Verlag, Stuttgart) and/or are known person skilled in the art, and under reaction conditions which are known and suitable for the said reactions. Use can also be made here of variants known per se which are not mentioned here in greater detail.

Depending on the conditions used, the reaction time is between a few minutes and 14 days, the reaction temperature is between −78° C. and 150° C., normally between −20° C. and 100° C., particularly preferably between 0° C. and 70° C.

The reaction is carried out in an inert solvent and generally in the presence of an acid-binding agent, preferably an organic base, such as DIPEA, triethylamine, dimethylaniline, pyridine, quinoline, piperidine or diethanolamine. The addition of an alkali-metal or alkaline-earth metal hydroxide, carbonate or bicarbonate or another salt of a weak acid of the alkali or alkaline-earth metals, preferably of potassium, sodium, calcium or caesium, may also be favourable. Suitable bases are metal oxides, such as, for example, aluminium oxide, alkali-metal hydroxides (including potassium hydroxide, sodium hydroxide and lithium hydroxide), alkaline-earth metal hydroxides (for example barium hydroxide and calcium hydroxide) and alkali-metal alkoxides (for example potassium ethoxide and sodium propoxide).

Suitable inert solvents are, inter alia, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to THF, glycol ethers, such as ethylene glycol monomethyl ether, dichloromethane and/or DMF.

The process and the subsequent work-up of the reaction mixture can basically be carried out as batch reaction or in continuous reaction manner. The continuous reaction manner comprises, for example, the reaction in a continuous stirred-tank reactor, a stirred-reactor cascade, a loop or cross-flow reactor, a flow tube or in a microreactor. The reaction mixtures are optionally worked up, as required, by filtration via solid phases, chromatography, separation between immiscible phases (for example extraction), adsorption on solid supports, distilling-off of solvents and/or azeotropic mixtures, selective distillation, sublimation, crystallisation, co-crystallisation or by nanofiltration on membranes.

The compounds of the formula (I) can preferably be obtained by carrying out a benzoin condensation. The present invention thus also relates to a process for the preparation and/or making-ready of compounds of the formula (I), part-formulae thereof and/or physiologically acceptable salts, tautomers, stereoisomers and/or solvates thereof, including mixtures thereof in all ratios, having the following steps:

(a) reaction of a furfural derivative of the formula (II)

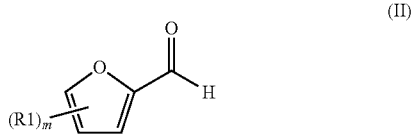

in which R1 and m have the meaning indicated above, with a furfural derivative of the formula (III)

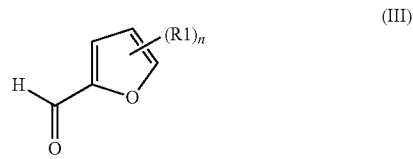

in which R1 and n have the meaning indicated above, in a benzoin addition to give compounds of the formula (I)

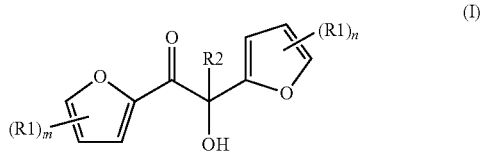

in which R1, m and n have the meaning indicated above, and optionally (b) conversion of a base or acid of the compounds of the formula (I) into one of their physiologically acceptable salts, and/or (c) apparent making-ready of the compounds of the formula (I) or one of their physiologically acceptable salts for the use according to the invention.

It preferably goes without saying that only step (b) is optional, while step (c) is obligatory and follows either step (a) or the optional step (b). In another embodiment, the invention also relates to a process for the preparation and optional making-ready of compounds of the formula (I), part-formulae thereof and/or physiologically acceptable salts, tautomers, stereoisomers and/or solvates thereof, including mixtures thereof in all ratios, for use in the prophylaxis, therapy and/or progress control of pigment disorders of the skin, having the above-mentioned steps, where step (c) is optional, but preferably obligatory.

The starting compounds are generally known. If they are novel, they can be prepared by methods known per se. The compounds of the formulae (II) and (III) can be prepared by known methods. If desired, the starting materials can be formed in situ, so that they are not isolated from the reaction mixture, but instead are immediately converted further into the compounds according to the invention. It is likewise possible to carry out the reaction stepwise.

The said compounds according to the invention can be used in their final non-salt form. On the other hand, the present invention also encompasses the use of these compounds in the form of their physiologically acceptable salts, which can be derived from various organic and inorganic acids and bases by procedures known in the art. Physiologically acceptable salt forms of the compounds of the formula (I) and part-formulae thereof are for the most part prepared by conventional methods. If the compounds contain a carboxyl group, one of its suitable salts can be formed by reacting the compound with a suitable base to give the corresponding base-addition salt. Such bases are, for example, alkali-metal hydroxides (for example potassium hydroxide, sodium hydroxide and lithium hydroxide), alkaline-earth metal hydroxides (for example barium hydroxide and calcium hydroxide), alkali-metal alkoxides (for example potassium ethoxide and sodium propoxide) and various organic bases, such as piperidine, diethanolamine and N-methylglutamine. A base of the formula (I) and part-formulae thereof can be converted into the associated acid-addition salt using an acid, for example by reaction of equivalent amounts of the base and the acid in an inert solvent, such as, for example, ethanol, with subsequent evaporation. Suitable acids for this reaction are, in particular, those which give physiologically acceptable salts, such as, for example, hydrogen halides (for example hydrogen chloride, hydrogen bromide or hydrogen iodide), other mineral acids and corresponding salts thereof (for example sulfate, nitrate or phosphate and the like), alkyl- and monoarylsulfonates (for example ethanesulfonate, toluenesulfonate and benzenesulfonate) and other organic acids and corresponding salts thereof (for example acetate, trifluoroacetate, tartrate, maleate, succinate, citrate, benzoate, salicylate, ascorbate and the like. Salts with physiologically unacceptable acids, for example picrates, can be used for the isolation and/or purification of the compounds of the formula (I).

It goes without saying that the salts in the sense of the invention can be based on the carboxylate groups as are present in the compounds of the formula (I) in that their acidic proton can be replaced by a metal. Alternatively, the salts in the sense of the invention can also be based on compounds of the formula (I) in which the proton on the alcohol function of the furoin derivatives has been replaced by an ion. This can be monovalent ions, such as, for example, $Li^+$, $Na^+$, $K^+$ or $NH_4^+$, but also polyvalent ions, giving salts of the $(furoin)_2M$ or $(furoin)_3M_2$ etc. type.

With regard to that stated above, it can be seen that the expression "physiologically acceptable salt" in the present connection is taken to mean an active compound which comprises a compound of the formula (I) in the form of one of its salts, in particular if this salt form imparts improved cosmetic and/or pharmacokinetic properties on the active compound compared with the free form of the active compound. The physiologically acceptable salt form of the active compound can also provide this active compound for the first time with a desired cosmetic and/or pharmacokinetic property and can even have a positive influence on the pharmacodynamics of this active compound with respect to its therapeutic efficacy in the body. Preferred salts in the sense of the invention are the lithium, sodium, potassium, magnesium, calcium, zinc, copper and ammonium salts of the compounds of the formula (I).

The compounds of the formula (I) may be chiral owing to their molecular structure and may accordingly occur in various enantiomeric forms. They may therefore be in racemic or optically active form. Since the cosmetic and/or pharmaceutical efficacy of the racemates or stereoisomers of the compounds of the formula (I) may differ, it may be desirable to use the enantiomers. In these cases, the end product, or even the intermediate, may be separated into enantiomeric compounds by chemical or physical measures known to the person skilled in the art or already employed as such in the synthesis.

It goes without saying that the apparent making-ready is directed to the use in the sense of the invention, i.e. for use in the lightening of skin, for use in the inhibition of tyrosinase, for use in the prophylaxis, therapy and/or progress control of pigment disorders of the skin and/or for the reduction of contrast differences in the skin shade which are caused by areas pigmented to different degrees. The apparent or obvious making-ready can consist, for example, in: a) particular design of the substance or matter, i.e. if these are individualised in such a way that suitability for the use in accordance with the patent is clearly evident; b) enclosure of use instructions (for example pack leaflet) on sale; c) formulation, making-up, dosing and ready-to-use packaging; d) therapy plan, dose recommendation; e) use of a use-specific product designation (Schulte/Kühnen, PatG [German Patents Act], 8th Edition, §14 marginal note 101).

The present invention furthermore relates to a preparation comprising at least one compound of the formula (I), part-formula (IA), (IB), (IC) and/or physiologically acceptable salts, tautomers, stereoisomers and/or solvates thereof, including mixtures thereof in all ratios, for the use according to the invention and to a vehicle which is suitable for cosmetic, pharmaceutical or dermatological applications and optionally physiologically acceptable assistants and/or fillers. For the purposes of the present invention, the term "agent", "composition" or "formulation" is also used synonymously alongside the term "preparation". The preparations here are usually preparations which can be applied topically, such as, for example, cosmetic or dermatological formulations or medical products. Can be applied topically in the sense of the invention means that the preparation is applied externally and locally, i.e. that the preparation must be suitable, for example, for being able to be applied to the skin. In this case, the preparations comprise a cosmetically, pharmaceutically or dermatologically suitable vehicle and, depending on the desired property profile, optionally further suitable ingredients. The topical preparations are preferably employed as cosmetic or dermatological preparation, particularly preferably as cosmetic preparation. Suitable vehicles and assistants or fillers are described in detail in the following part.

The preparations may include or comprise, essentially consist of or consist of the necessary or optional constituents mentioned above and/or below. All compounds or components which can be used in the preparations are either known and commercially available or can be synthesised by known processes. Further preferred combinations of embodiments are disclosed in the Claims.

The compound of the formula (I), as indicated above and also as preferably described, and/or physiologically acceptable salts, tautomers, stereoisomers and/or solvates thereof, including mixtures thereof in all ratios, are present in the preparation of the invention in an amount of 0.0001 to 20% by weight, based on the total weight of the preparation. An amount of 0.0001 to 15% by weight is preferably employed, particularly preferably 0.0001 to 10% by weight, very particularly preferably 0.0001 to 5% by weight. The person skilled in the art is presented with absolutely no difficulties in selecting appropriately the amounts depending on the intended effect of the preparation.

It is furthermore advisable for the compound of the formula (I), part-formulae thereof and/or physiologically acceptable salts, tautomers, stereoisomers and/or solvates thereof, including mixtures thereof in all ratios, to be present in the preparation of the invention in combination with at least one further active compound. The further active compound is preferably selected from the group of UV filters, antioxidants, vitamins, skin-lightening active compounds, anti-ageing active compounds, anti-inflammatory active compounds, antimicrobial active compounds, active compounds for improving the moisture content of the skin (skin-moisture regulators), anticellulite active compounds, antiwrinkle active compounds, anti-dandruff active compounds, anti-acne active compounds, deodorants, pigments and self-tanning substances, particularly preferably from the group of UV filters, antioxidants, vitamins, skin-lightening active compounds, anti-ageing active compounds and anticellulite active compounds.

Preparations which are preferred in accordance with the invention also comprise one or more UV filters besides at least one compound of the formula (I). In principle, all UV filters are suitable for combination with the compounds of the formula (I) or part-formulae thereof in the preparation according to the invention. Particular preference is given to UV filters whose physiological acceptability has already been demonstrated. There are many proven substances known from the specialist literature both for UVA and also UVB filters. The compounds shown in the following lists should only be regarded as examples. Other UV filters can of course also be used.

Besides the compounds of the formula (I) and the optional other ingredients, preferred preparations may comprise organic UV filters, so-called hydrophilic or lipophilic sun-protection filters, which are effective in the UVA region and/or UVB region and/or IR and/or VIS region (absorbers). These substances can be selected, in particular, from p-aminobenzoic acid derivatives, salicylic acid derivatives, β,β-diphenylacrylate derivatives, camphor derivatives, triazine derivatives, cinnamic acid derivatives and polymeric filters and silicone filters, which are described in the application WO 93/04665. Further examples of organic filters are indicated in the patent application EP-A 0 487 404. The said UV filters are usually named below in accordance with INCI nomenclature. Particularly suitable for a combination are:

para-aminobenzoic acid and derivatives thereof: PABA, Ethyl PABA, Ethyl dihydroxy-propyl PABA, Ethylhexyl dimethyl PABA, for example marketed by ISP under the name "Escalol 507", Glyceryl PABA, PEG-25 PABA, for example marketed by BASF under the name "Uvinul P25".

Salicylates: Homosalate marketed by Merck under the name "Eusolex HMS"; Ethylhexyl salicylate, for example marketed by Symrise under the name "Neo Heliopan OS"; Dipropylene glycol salicylate, for example marketed by Scher under the name "Dipsal"; TEA salicylate, for example marketed by Symrise under the name "Neo Heliopan TS".

β,β-Diphenylacrylate derivatives: Octocrylene, for example marketed by Merck under the name "Eusolex® OCR"; "Uvinul N539" from BASF; Etocrylene, for example marketed by BASF under the name "Uvinul N35".

Benzophenone derivatives: benzophenone-1, for example marketed under the name "Uvinul 400"; benzophenone-2, for example marketed under the name "Uvinul D50"; benzophenone-3 or oxybenzone, for example marketed under the name "Uvinul M40"; benzophenone-4, for example marketed under the name "Uvinul MS40"; benzophenone-9, for example marketed by BASF under the name "Uvinul DS-49"; benzophenone-5, benzophenone-6, for example marketed by Norquay under the name "Helisorb 11"; benzophenone-8, for example marketed by American Cyanamid under the name "SpectraSorb UV-24"; benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-benzylidenecamphor, for example marketed by Chimex under the name "Mexoryl SD"; 4-methylbenzylidenecamphor, for example marketed by Merck under the name "Eusolex 6300"; benzylidenecamphorsulfonic acid, for example marketed by Chimex under the name "Mexoryl SL"; Camphor benzalkonium methosulfate, for example marketed by Chimex under the name "Mexoryl SO"; terephthalylidenedicamphorsulfonic acid, for example marketed by Chimex under the name "Mexoryl SX"; polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232"; disodium phenyl dibenzimidazole tetrasulfonate, for example marketed by Symrise under the name "Neo Heliopan AP".

Phenylbenzotriazole derivatives: Drometrizol trisiloxane, for example marketed by Rhodia Chimie under the name "Silatrizole"; Methylenebis(benzotriazolyl)tetramethylbutylphenol in solid form, for example marketed by Fairmount Chemical under the name "MIXXIM BB/100", or in micronised form as an aqueous dispersion, for example marketed by BASF under the name "Tinosorb M".

Triazine derivatives: Ethylhexyltriazone, for example marketed by BASF under the name "Uvinul T150"; Diethylhexylbutamidotriazone, for example marketed by Sigma 3V under the name "Uvasorb HEB"; 2,4,6-tris (diisobutyl 4'-aminobenzalmalonate)s-triazine or 2,4,6-Tris(biphenyl)-1,3,5-triazine marketed by BASF as Tinosorb A2B; 2,2'-[6-(4-methoxyphenyl)-1,3,5-triazine-2,4-diyl]bis[5-(2-ethylhexyl)oxy]phenol; marketed by BASF as Tinosorb S; N2,N4-bis[4-[5-(1,1-dimethylpropyl)-2-benzoxazolyl]phenyl]-N-6-(2-ethylhexyl)-1,3,5-triazine-2,4,6-triamine marketed as Uvasorb K 2A by Sigma 3V.

Anthraniline derivatives: Menthyl anthranilate, for example marketed by Symrise under the name "Neo Heliopan MA".

Imidazole derivatives: ethylhexyldimethoxybenzylidenedioxoimidazoline propionate.

Benzalmalonate derivatives: polyorganosiloxanes containing functional benzalmalonate groups, such as, for example, Polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl)benzoxazol-2-yl(4-phenyl) imino]-6-(2-ethylhexyl)imino-1,3,5-triazine, for example marketed by Sigma 3V under the name Uvasorb K2A, and mixtures comprising this Piperazine derivatives, for example the compound

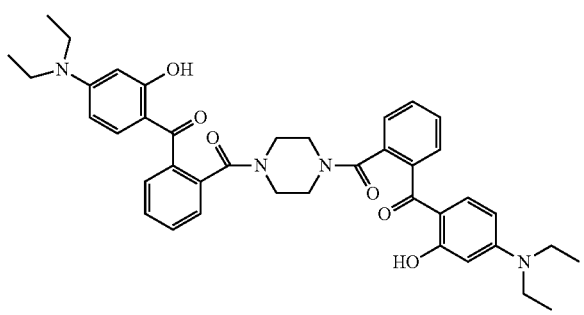 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

or the UV filters of the following structures

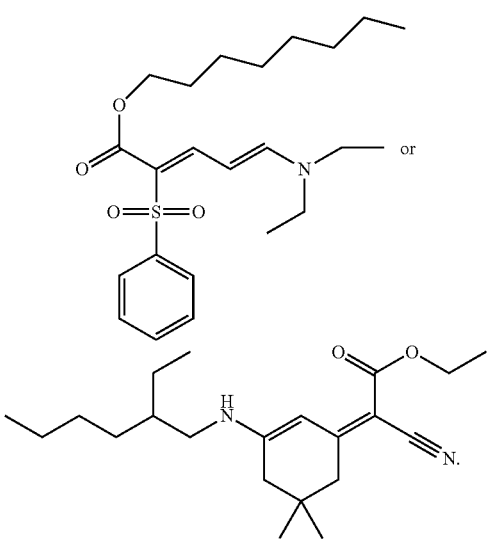

It is also possible to use UV filters based on polysiloxane copolymers having a random distribution in accordance with the following formula, where, for example, a=1.2; b=58 and c=2.8:

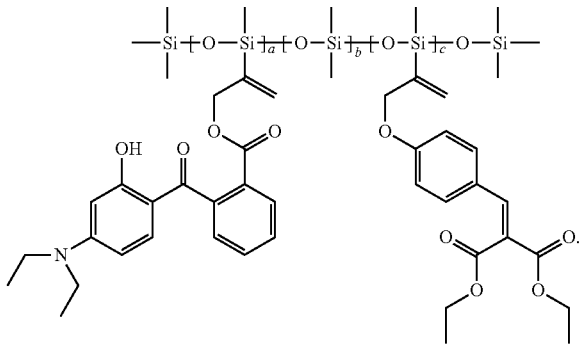 [SMILES: C=C(COC(=O)c1ccccc1C(=O)c1ccc(N(CC)CC)cc1O)[Si](C)(O[Si](C)(C)C)O[Si](C)(C)O[Si](C)(O[Si](C)(C)C)C(=C)COc1ccc(C=C(C(=O)OCC)C(=O)OCC)cc1]

Suitable organic UV-protecting substances can preferably be selected from the following list: Ethylhexyl salicylate, phenylbenzimidazolesulfonic acid, benzophenone-3, benzophenone-4, benzophenone-5, n-Hexyl 2-(4-diethylamino-2-hydroxybenzoyl)benzoate, 4-methylbenzylidenecamphor, terephthalylidenedicamphorsulfonic acid, disodium phenyldibenzimidazoletetrasulfonate, methylenebis(benzotriazolyl)tetramethylbutylphenol, Ethyl-hexyltriazone, Diethylhexylbutamidotriazone, Drometrizole trisiloxane, Polysilicone-15, 1,1-Dicarboxy(2,2'-dimethylpropyl)-4,4-diphenylbutadiene, 2,4-Bis[5-1 (dimethylpropyl)benzoxazol-2-yl(4-phenyl) imino]-6-(2-ethylhexyl)imino-1,3,5-triazine and mixtures thereof.

These organic UV filters are generally incorporated into formulations in an amount of 0.01 to 20 percent by weight, preferably 1 to 20% by weight.

Besides the compounds of the formula (I) and the optional other organic UV filters, as described above, the preparations may comprise further inorganic UV filters, so-called particulate UV filters. These combinations with particulate UV filters are possible both as powder and also as dispersion or paste of the following types. Preference is given here both to those from the group of the titanium dioxides, such as, for example, coated titanium dioxide (for example Eusolex® T-2000, Eusolex® T-AQUA, Eusolex® T-AVO, Eusolex® T-OLEO), zinc oxides (for example Sachtotec®), iron oxides or also cerium oxides and/or zirconium oxides. Furthermore, combinations with pigmentary titanium dioxide or zinc oxide are also possible, where the particle size of these pigments is greater than or equal to 200 nm, for example Hombitan® FG or Hombitan® FF-Pharma.

It may furthermore be preferred for the preparations to comprise inorganic UV filters which have been aftertreated by conventional methods, as described, for example, in Cosmetics & Toiletries 1990, 105, 53. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

Particulate UV filters which are preferably employed here are:
Untreated titanium dioxides, such as, for example, the products Microtitanium Dioxide MT 500 B from Tayca; titanium dioxide P25 from Degussa;
Aftertreated micronised titanium dioxides with aluminium oxide and silicon dioxide aftertreatment, such as, for example, the product "Microtitanium Dioxide MT 100 SA from Tayca, or the product "Tioveil Fin" from Uniqema;
Aftertreated micronised titanium dioxides with aluminium oxide and/or aluminium stearate/laurate aftertreatment, such as, for example, Microtitanium Dioxide MT 100 T from Tayca; Eusolex T-2000 from Merck;
Aftertreated micronised titanium dioxides with iron oxide and/or iron stearate aftertreatment, such as, for example, the product "Microtitanium Dioxide MT 100 F" from Tayca;
Aftertreated micronised titanium dioxides with silicon dioxide, aluminium oxide and silicone aftertreatment, such as, for example, the product "Microtitanium Dioxide MT 100 SAS", from Tayca;
Aftertreated micronised titanium dioxides with sodium hexametaphosphate, such as, for example, the product "Microtitanium Dioxide MT 150 W" from Tayca.

The treated micronised titanium dioxides employed for the combination may also be aftertreated with:
Octyltrimethoxysilanes, such as, for example, the product Tego Sun T 805 from Degussa;
Silicon dioxide; such as, for example, the product Parsol T-X from DSM;
Aluminium oxide and stearic acid; such as, for example, the product UV-Titan M160 from Sachtleben;
Aluminium and glycerine; such as, for example, the product UV-Titan from Sachtleben,
Aluminium and silicone oils, such as, for example, the product UV-Titan M262 from Sachtleben;
Sodium hexamethaphosphate and polyvinylpyrrolidone,
Polydimethylsiloxanes, such as, for example, the product 70250 Cardre UF TiO2SI3" from Cardre;
Polydimethylhydrogenosiloxanes, such as, for example, the product Microtitanium Dioxide USP Grade Hydrophobic" from Color Techniques.

The combination with the following products may furthermore also be advantageous:
Untreated zinc oxides, such as, for example, the product Z-Cote from BASF (Sunsmart), Nanox from Elementis;
Aftertreated zinc oxides, such as, for example, the following products:
"Zinc Oxide CS-5" from Toshibi (ZnO aftertreated with polymethylhydrogeno-siloxane);
Nanogard Zinc Oxide FN from Nanophase Technologies;
"SPD-Z1" from Shin-Etsu (ZnO aftertreated with a silicone-grafted acrylic polymer, dispersed in cyclodimethylsiloxanes);
"Escalol Z100" from ISP (aluminium oxide-aftertreated ZnO, dispersed in an ethylhexyl methoxycinnamate/PVP-hexadecene/methicone copolymer mixture);
"Fuji ZNO-SMS-10" from Fuji Pigment (ZnO aftertreated with silicon dioxide and polymethylsilesquioxane);
Untreated cerium oxide micropigment, for example with the name "Colloidal Cerium Oxide" from Rhone Poulenc;
Untreated and/or aftertreated iron oxides with the name Nanogar from Arnaud.

By way of example, it is also possible to employ mixtures of various metal oxides, such as, for example, titanium dioxide and cerium oxide, with and without aftertreatment, such as, for example, the product Sunveil A from Ikeda. In addition, mixtures of aluminium oxide-, silicon dioxide- and silicone-aftertreated titanium dioxide/zinc oxide mixtures, such as, for example, the product UV-Titan M261 from Sachtleben, can also be employed.

These inorganic UV filters are generally incorporated into the preparations in an amount of 0.1 to 25 percent by weight, preferably 2 to 10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form. The capsules in preparations to be employed in accordance with the invention are preferably present in amounts which ensure that the encapsulated UV filters are present in the preparation in the percent by weight ratios indicated above.

A further preferred embodiment of the invention relates to the combination of the compounds of the formula (I) with at least one substance which serves for maintaining and/or improving the moisture content of the skin. These substances can, without this being intended to be regarded as a restriction, also be, inter alia, substances which belong to the so-called natural moisturising factors, such as, for example, 2-oxopyrrolidine 5-carboxylic acid.

In a further preferred embodiment of the invention, the preparation comprises one or more antioxidants and/or one or more vitamins. The use of antioxidants enables a protective action against oxidative stress or against the effect of free radicals in general to be achieved, the person skilled in the art being presented with absolutely no difficulties in selecting antioxidants which act suitably quickly or with a time delay. There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as, for example, D,L-carnosine, D-carnosine, L-carnosine and derivatives thereof (for example anserine), carotinoids, carotenes (such as, for example, α-carotene, β-carotene, lycopene) and derivatives thereof, chlorogenic acid and derivatives thereof, lipoic acid and derivatives thereof (such as, for example, dihydrolipoic acid), aurothioglucose, propylthiouracil and other thiols (such as, for example, thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (such as, for example, esters, ethers, peptides, lipids, nucleotides, nucleosides and salts), and sulfoximine compounds (such as, for example, buthionine sulfoximines, homocysta sulfoximine, buthionine sulfones, penta-, hexa- and heptathionine sulfoximine) in very low tolerated doses (such as, for example, pmol to μmol/kg), and also (metal) chelating agents, (such as, for example, α-hydroxyfatty acids, palmitic acid, phytic acid, lactoferrin), α-hydroxy acids (such as, for example, citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (such as, for example, ascorbyl palmitate, magnesium ascorbyl phosphate, ascorbyl acetate), tocopherols and derivatives (such as, for example, vitamin E acetate), vitamin A and derivatives (such as, for example, vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (such as, for example, ZnO, ZnSO$_4$), selenium and derivatives thereof (such as, for example, selenomethionine), stilbenes and derivatives thereof (such as, for example, stilbene oxide, trans-stilbene oxide). Further suitable antioxidants are also described in WO 2006/111233 and WO 2006/111234.

Suitable antioxidants are also compounds of the general formulae A or B

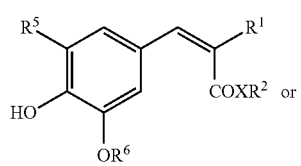

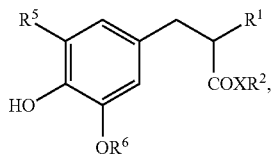

in which
R$^1$ denotes —C(O)CH$_3$, —CO$_2$R$^3$, —C(O)NH$_2$ or —C(O)N(R$^4$)$_2$,
X denotes O or NH,
R$^2$ denotes linear or branched alkyl having 1 to 30 C atoms,
R$^3$ denotes linear or branched alkyl having 1 to 20 C atoms,
R$^4$ denotes H or linear or branched alkyl having 1 to 8 C atoms,
R$^5$ denotes H, linear or branched alkyl having 1 to 8 C atoms or linear or branched alkoxy having 1 to 8 C atoms, and
R$^6$ denotes linear or branched alkyl having 1 to 8 C atoms.

Preference is given to derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (such as, for example, Oxynex® ST Liquid) and/or bis(2-ethylhexyl) 2-(4-hydroxy-3,5-dimethoxybenzy)malonate (such as, for example, RonaCare® AP).

Mixtures of antioxidants are likewise suitable for use in the preparations according to the invention. Known and commercial mixtures are, for example, mixtures comprising, as active ingredients, lecithin, L-(+)-ascorbyl palmitate and citric acid (such as, for example, Oxynex® AP), natural tocopherols, L-(+)-ascorbyl palmitate, L-(+)-ascorbic acid and citric acid (such as, for example, Oxynex® K LIQUID), tocopherol extracts from natural sources, L-(+)-ascorbyl palmitate, L-(+)-ascorbic acid and citric acid (such as, for example, Oxynex® L LIQUID), DL-α-tocopherol, L-(+)-ascorbyl palmitate, citric acid and lecithin (such as, for example, Oxynex® LM) or butylhydroxytoluene (BHT), L-(+)-ascorbyl palmitate and citric acid (such as, for example, Oxynex® 2004). Antioxidants of this type are usually employed in such compositions with compounds of the formula (1) or part-formulae thereof in percent by weight ratios in the range from 1000:1 to 1:1000, preferably in percent by weight ratios of 100:1 to 1:100.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. Lemanska et al., Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3'4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-penta-hydroxyflavone) is frequently mentioned as a particularly effective antioxidant (for example Rice-Evans et al., Trends in Plant Science 1997, 2(4), 152-159). Lemanska et al., Free Radical Biology & Medicine 2001, 31(7), 869-881, have investigated the pH dependence of the antioxidant action of hydroxyflavones.

Quercetin exhibits the highest activity amongst the structures investigated over the entire pH range.

The preparations according to the invention may comprise vitamins as further ingredients. Vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin K1, esculin (vitamin P active compound), thiamine (vitamin $B_1$), nicotinic acid (niacin), pyridoxine, pyridoxal, pyridoxamine, (vitamin $B_6$), panthothenic acid, biotin, folic acid and cobalamine (vitamin $B_{12}$) are preferably present in the preparations according to the invention, particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the preparations in ranges from 0.01 to 5% by weight, based on the total weight. Nutrition-physiological applications are oriented towards the respective recommended vitamin requirement.

The preparations according to the invention may also comprise one or more further skin-lightening active compounds or synonymously depigmentation active compounds. Skin-lightening active compounds can in principle be all active compounds known to the person skilled in the art. Suitable for combination are commercially available melanogenesis inhibitors, such as, for example, ascorbic acid and derivatives thereof, aloesin, niacinamide, emblica, elagic acid, liquorice extract, mulberry extract, kojic acid, liquorice extract, rucinol, hydroquinone, azelaic acid, arbutin, magnesium ascorbyl phosphate or the like. Preferred examples of compounds having skin-lightening activity are hydroquinone, niacinamide, ascorbic acid and salts thereof, kojic acid, arbutin, aloesin, azelaic acid, elagic acid or rucinol. Preferred examples of extracts having skin-lightening activity are liquorice extract, mulberry extract or emblica.

The preparations according to the invention may in addition comprise anti-ageing active compounds, anticellulite active compounds or conventional skin-protecting or skin-care active compounds. Skin-protecting or skin-care active compounds can in principle be all active compounds known to the person skilled in the art. Particularly preferred anti-ageing active compounds are pyrimidinecarboxylic acids, aryl oximes, bioflavonoids, bioflavonoid-containing extracts, chromones or retinoids.

Suitable anti-ageing active compounds, in particular for skin-care preparations, are preferably also so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidinecarboxylic acids (such as ectoin and hydroxyectoin), proline, betaine, glutamine, cyclic diphosphoglycerate, N-acetyl-ornithine, trimethylamine N-oxide, di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof.

Additionally, anti-ageing active compounds which can be used are products from Merck, such as, for example, 5,7-dihydroxy-2-methylchromone, marketed under the trade name RonaCare® Luremine, Ronacare® Isoquercetin, Ronacare® Tilirosid or Ronacare® Cyclo-peptide 5.

Known anti-ageing substances are also chromones, as described, for example, in EP 1508327, or retinoids, for example retinol (vitamin A), retinoic acid, retinaldehyde or also synthetically modified compounds of vitamin A. The chromones and retinoids described are simultaneously also effective anticellulite active compounds. An anticellulite active compound which is likewise known is caffeine.

The invention likewise relates to a preparation comprising at least one compound of the formula (I), as described above, and a self-tanning substance which has a contrast-reduction effect and achieves a uniform skin shade. The invention likewise relates to the use of compounds of the formula (I), as described, in combination with self-tanning substances for contrast reduction and achieving a uniform skin shade. A contrast-reduction agent is accordingly a substance which reduces a non-uniform skin coloration by reducing the contrast between more strongly and less strongly coloured skin areas. An under-uniform skin coloration of this type can arise here through non-uniform pigmentation and/or a different distribution of the horny skin. Non-uniform pigmentation is by no means unusual in the population and is based on different levels of melanin production by the melanocytes or an irregular distribution of the melanocytes in the skin. The combination of tanning mixtures which are based on the Maillard reaction or Michael addition with melanogenesis-inhibiting substances has the effect that skin areas which are already hyperpigmented lose their high melanin concentration, and the skin shade generated at the skin surface by the colorant becomes established over a large area.

A contrast reduction can be achieved, in particular, by preparations in which at least one compound of the formula (I) are additionally combined with a self-tanning substance, preferably comprising dihydroxyacetone (DHA) and derivatives derived therefrom, DHA rapid, DHA plus or erythrulose, or a mixture of self-tanning substances, preferably comprising DHA, DHA rapid, DHA plus and/or erythrulose. Advantageous self-tanners which can be employed, inter alia, in a dihydroxyacetone-containing mixture or preparation are: glycerolaldehyde, hydroxymethylglyoxal, γ-dialdehyde, 6-aldo-D-fructose, ninhydrin, 5-hydroxy-1,4-naphtoquinone (juglone) or 2-hydroxy-1,4-naphtoquinone (lawsone) or a mixture of the said compounds. Erythrulose is particularly preferably employed in the dihydroxyacetone-containing mixture.

The at least one compound of the formula (I) can also be used in accordance with the invention together with a mixture of self-tanning substances comprising at least dihydroxyacetone and a further self-tanner selected from the above-mentioned group. By way of example, the mixture to be used in accordance with the invention consists of dihydroxyacetone and at least one further self-tanning substance, as described above. This mixture can then be combined in accordance with the invention with at least one compound of the formula (I) and employed in cosmetic, dermatological or pharmaceutical preparations, as described below. Dihydroxyacetone or a derivative derived therefrom is very particularly preferably employed without further self-tanning substances.

In the preparations described, which, in accordance with the invention, comprise at least one compound of the formula (I) and a self-tanner, coloured pigments may furthermore also be present, where the layer structure of the pigments is not limited. On use of 0.5 to 5% by weight, the coloured pigment should preferably be skin-coloured or brownish. The selection of a corresponding pigment is familiar to the person skilled in the art.

The compositions or preparations described are particularly suitable for use in the lightening of skin, inhibition of tyrosinase and/or prophylaxis, therapy and/or progress control of pigment disorders of the skin, in all cases in particular in the case of hyperpigmentation, freckles, age spots, sun spots and environmentally induced skin ageing. They are present here in various administration forms which are usually used for this application. The following may be mentioned, for example, as application form of the preparations according to the invention: solutions, suspensions, emulsions, PIT emulsions, pastes, ointments, gels, creams, lotions, powders, soaps, surfactant-containing cleansing preparations, oils, aerosols, plasters, compresses, bandages and sprays, in particular for external application. Further application forms are, for example, sticks, shampoos and shower baths. Cosmetic and dermatological preparations according to the invention can be, in particular, a water-free preparation, a lotion or emulsion, such as cream or milk, or microemulsion, in each case of the water-in-oil (W/O) type or of the oil-in-water (O/W) type, a multiple emulsion, for example of the water-in-oil-in-water (W/O/W) type or vice versa (O/W/O), gels or solutions (in particular oily-alcoholic, oily-aqueous or aqueous-alcoholic gels or solutions), a solid stick, an ointment or an aerosol. For application, the cosmetic and dermatological preparations according to the invention are applied to the skin in adequate amount in the usual manner for cosmetics.

An embodiment of the invention is an emulsion which is in the form of a cream or milk and comprises, for example, fatty alcohols, fatty acids, fatty acid esters, in particular triglycerides of fatty acids, lanolin, natural and synthetic oils or waxes and emulsifiers in the presence of water. Further particularly preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids. A particularly preferred preparation according to the invention may also be in the form of an alcoholic gel which comprises one or more lower alcohols or polyols, such as ethanol, propylene glycol or glycerol, and a thickener, such as siliceous earth. The oily-alcoholic gels additionally comprise natural or synthetic oil or wax. The solid sticks preferably consist of natural or synthetic waxes and oils, fatty alcohols, fatty acids, fatty acid esters, lanolin and other fatty substances. If a preparation is formulated as an aerosol, the usual propellants, such as alkanes, air, nitrogen, dinitrogen monoxide, particularly preferably alkanes or air, are preferably used.

The one or more compounds of the formula (I), as described, can be incorporated into cosmetic or dermatological preparations in the usual manner. The preparation is, for example, designed in such a way that it is suitable for oral administration. It is also advantageous to administer ectoins in encapsulated form, for example in collagen matrices and other conventional encapsulation materials, such as, for example, as cellulose or chitin capsules, in gelatine or wax matrices or encapsulated liposomally. In particular, wax matrices, as described in DE-A-4308282, have proven favourable.

The preparations may include or comprise, essentially or consist of the said necessary or optional constituents or ingredients. All compounds or components which can be used in the preparations are either known and commercially available or can be synthesised by known processes. Any desired conventional vehicles, assistants and, if desired, further active compounds may be added to the preparation. Preferred assistants originate from the group of the preservatives, stabilisers, solubilisers, colorants, i.e. pigments, dyes, emulsifiers or odour improvers.

Ointments, pastes, creams and gels may comprise the customary vehicles which are suitable for topical application, such as, for example, animal and vegetable fats, waxes, paraffins, starch, tragacanth, cellulose derivatives, polyethylene glycols, silicones, bentonites, silica, talc and titanium dioxide, or mixtures of these substances. Powders and sprays may comprise the customary vehicles, such as, for example, lactose, talc, silica, aluminium hydroxide, calcium silicate and polyamide powder, or mixtures of these substances. Sprays may additionally comprise the customary readily volatile, liquefied propellants, such as, for example, chlorofluorocarbons, propane/butane or dimethyl ether. Compressed air can also advantageously be used. However, air can also be employed in pressureless metering devices, such as, for example, pump sprays. Solutions and emulsions may comprise the customary vehicles, such as solvents, solubilisers and emulsifiers, such as, for example, water, ethanol, isopropanol, ethyl carbonate, ethyl acetate, benzyl alcohol, benzyl benzoate, propylene glycol, 1,3-butyl glycol, oils, in particular cottonseed oil, peanut oil, wheat-germ oil, olive oil, castor oil and sesame oil, glycerol fatty acid esters, polyethylene glycols and fatty acid esters of sorbitan, or mixtures of these substances; a preferred solubiliser in general is 2-isopropyl-5-methylcyclohexanecarbonyl-D-alanine methyl ester. Suspensions may comprise the customary vehicles, such as liquid diluents, such as, for example, water, ethanol or propylene glycol, suspension media, such as, for example, ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances. Soaps may comprise the customary vehicles, such as alkali-metal salts of fatty acids, salts of fatty acid monoesters, fatty acid protein hydrolysates, isothionates, lanolin, fatty alcohol, vegetable oils, plant extracts, glycerol, sugars, or mixtures of these substances. Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamido-betaines, fatty alcohols, fatty acid glycerides, fatty acid diethanolamides, vegetable and synthetic oils, lanolin derivatives, ethoxylated glycerol fatty acid esters, or mixtures of these substances. Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

The preferred preparation forms according to the invention include, in particular, emulsions. O/W emulsions are particularly preferred. Emulsions, W/O emulsions and O/W emulsions can be obtained in a conventional manner. Emulsions according to the invention are advantageous and comprise, for example, the said fats, oils, waxes and other fatty substances, as well as water or an aqueous phase, for example with solvents or hydrophilic surfactants, and an emulsifier, as usually used for a preparation of this type.

The lipid phase may advantageously be selected from the following substance groups:
mineral oils, mineral waxes;
oils, such as, for example, triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes, and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, from the group of the esters of aromatic carboxylic acid and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, such as, for example, jojoba oil. Furthermore, the oil phase can advantageously be selected from the group of branched and unbranched hydrocarbons and hydrocarbon waxes, silicone oils, dialkyl ethers, the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides can advantageously be selected, for example, from the group of synthetic, semi-synthetic and natural oils, for example olive oil, sunflower oil, soya oil, peanut oil, rapeseed oil, almond oil, palm oil, coconut oil, palm kernel oil and the like. Any desired mixtures of oil and wax components of this type may also advantageously be employed for the purposes of the present invention. It may also be advantageous to employ waxes, for example cetyl palmitate, as sole lipid component of the oil phase.

The aqueous phase of the preparations according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, such as, for example, ethanol, isopropanol, 1,2-propanediol, glycerol, and, in particular, one or more thickeners, which may advantageously be selected from the group of silicon dioxide, aluminium silicates, polysaccharides or derivatives thereof, such as, for example, hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination. In particular, mixtures of the above-mentioned solvents are used. In the case of alcoholic solvents, water may be a further constituent.

In a preferred embodiment, the preparations according to the invention comprise hydrophilic surfactants. The hydrophilic surfactants are preferably selected from the group of the alkylglucosides, acyl lactylates, betaines and coconut amphoacetates.

Emulsifiers that can be used are, for example, the known W/O and O/W emulsifiers. It is advantageous to use further conventional co-emulsifiers in the preferred O/W emulsions according to the invention.

The co-emulsifiers selected in accordance with the invention are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R', or if isoalkyl derivatives are present, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols).

It is furthermore advantageous to select the fatty acid ethoxylates from the following group: polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth1-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/cprinate, polyethylene glycol (20) glyceryl oleate, polyethylene glycol (20) glyceryl isostearate, polyethylene glycol (18) glyceryl oleate (cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate and polyethylene glycol (20) sorbitan monooleate.

The following can be employed as optional W/O emulsifiers, but ones which may nevertheless be advantageous in accordance with the invention: fatty alcohols having 8 to 30 carbon atoms, monoglycerol esters of saturated and/or unsaturated, branched and/or unbranched alkanecarboxylic acids having a chain length of 8 to 24, in particular 12 to 18 C atoms, diglycerol esters of saturated and/or unsaturated, branched and/or unbranched alkanecarboxylic acids having a chain length of 8 to 24, in particular 12 to 18 C atoms, monoglycerol ethers of saturated and/or unsaturated, branched and/or unbranched alcohols having a chain length of 8 to 24, in particular 12 to 18 C atoms, diglycerol ethers of saturated and/or unsaturated, branched and/or unbranched alcohols having a chain length of 8 to 24, in particular 12 to 18 C atoms, propylene glycol esters of saturated and/or unsaturated, branched and/or unbranched alkanecarboxylic acids having a chain length of 8 to 24, in particular 12 to 18 C atoms, and sorbitan esters of saturated and/or unsaturated, branched and/or unbranched alkanecarboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG-30 dipolyhydroxystearate.

The preparation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments, which colour the composition itself or the skin, and other ingredients usually used in cosmetics.

The dispersant or solubiliser used can be an oil, wax or other fatty substances, a lower monoalcohol or a lower polyol or mixtures thereof. Particularly preferred monoalcohols or polyols include ethanol, i-propanol, propylene glycol, glycerol and sorbitol.

The invention also relates to a process for the preparation and optional making-ready of a preparation according to the invention having the following steps: (a) mixing of at least one compound of the formula (I), part-formula (IA), (IB), (IC) and/or physiologically acceptable salts, tautomers, stereoisomers and/or solvates thereof, including mixtures thereof in all ratios, with at least one further active compound and at least one vehicle which is suitable for topical applications and optionally with physiologically acceptable assistants and/or fillers, and optionally (b) apparent making-ready of the compounds of the formula (I). The preparations according to the invention can be prepared with the aid of techniques which are well known to the person skilled in the art. The mixing can result in dissolution, emulsification or dispersal of the at least one compound of the formula (I) or part-formula thereof, as described above, in the vehicle. The prior teaching of the invention and embodiments thereof relating to the compounds of the formula (I) and preparations therewith is valid and can be applied without restrictions to the preparation and optional making-ready of the preparation, if it appears appropriate.

The invention also relates to compounds of the formula (I)

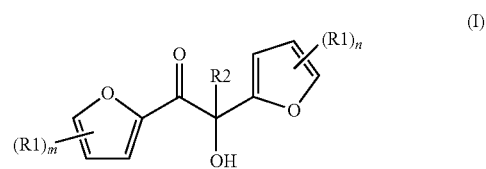

in which
R1 denotes A, Cyc, OH or Ar,
R2 denotes Y, Cyc, OH or Ar,
Y denotes H or Alk,
A denotes unbranched or branched alkyl having 5-18 C atoms, where, independently of one another, 1-3H atoms may be replaced by F and/or, independently of one another, one or two adjacent $CH_2$ groups may be replaced by —O—, —N(Alk)-, a —CH=CH— or —C≡C— group,
Alk denotes unbranched or branched alkyl having 1-12 C atoms,
Cyc denotes cyclic alkyl having 3-8 C atoms, where, independently of one another, 1-3H atoms may be replaced by F and/or, independently of one another, one or two adjacent $CH_2$ groups may be replaced by —O—, —N(Alk)- or a —CH=CH— group,
Ar denotes mono-, bi- or tricyclic aryl having 5 to 14 C atoms, which may be unsubstituted or mono-, di- or trisubstituted by F, Alk or —$(CY_2)_p$—OY, and
m, p, independently of one another, denote 0, 1 or 2,
with the proviso that Y and Ar are excluded for R2 if m and n simultaneously denote 0, and/or physiologically acceptable salts, tautomers, stereoisomers and/or solvates thereof, including mixtures thereof in all ratios.

A preferred embodiment of the invention relates to compounds of the part-formula (IC)

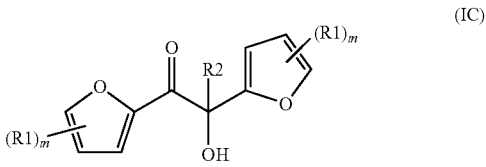

in which
R1 denotes A, Cyc, OH or Ar,
R2 denotes Y, Cyc, OH or Ar,
Y denotes H or Alk,
A denotes unbranched or branched alkyl having 5-8 C atoms, where, independently of one another, 1-3H atoms may be replaced by F and/or, independently of one another, one or two adjacent $CH_2$ groups may be replaced by —O—, —N(Alk)-, a —CH=CH— or —C≡C— group,
Alk denotes unbranched or branched alkyl having 1-4 C atoms, Cyc denotes cyclic alkyl having 3-8 C atoms, where, independently of one another, 1-3H atoms may be replaced by F and/or, independently of one another, one or two adjacent $CH_2$ groups may be replaced by —O—, —N(Alk)- or a —CH=CH— group, Ar denotes mono-, bi- or tricyclic aryl having 5 to 14 C atoms, which may be unsubstituted or mono-, di- or trisubstituted by F, Alk or —$(CY_2)_p$—OY, and m, p, independently of one another, denote 0, 1 or 2, with the proviso that Y and Ar are excluded for R2 if m denotes 0, and/or physiologically acceptable salts, tautomers, stereoisomers and/or solvates thereof, including mixtures thereof in all ratios.

In a particularly preferred embodiment of the invention, compounds of the part-formula (10) are prepared in which R1 denotes A, Cyc or Ar, R2 denotes Cyc, Y denotes H or Alk, A denotes unbranched or branched alkyl having 5-8 C atoms, where, independently of one another, 1-3H atoms may be replaced by F and/or, independently of one another, one or two adjacent $CH_2$ groups may be replaced by a —CH=CH— or —C≡C— group, Alk denotes unbranched or branched alkyl having 1-4 C atoms, Cyc denotes cyclic alkyl having 3-8 C atoms, where, independently of one another, 1-3H atoms may be replaced by F and/or, independently of one another, one or two adjacent $CH_2$ groups may be replaced by a —CH=CH— group, Ar denotes mono-, bi- or tricyclic aryl having 5 to 14 C atoms, which may be unsubstituted or mono- or disubstituted by F or OY, and m denotes 0, 1 or 2, and/or physiologically acceptable salts, tautomers, stereoisomers and/or solvates thereof, including mixtures thereof in all ratios.

The invention furthermore also relates to a process for the preparation of compounds of the part-formula (IC) and/or salts, tautomers, stereoisomers and/or solvates thereof, including mixtures thereof in all ratios, having the following steps:

(a) benzoin addition of furfural derivatives of the formula (II)

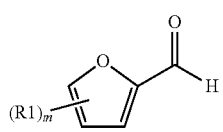

(II)

in which R1 and m have the meaning indicated above, to give compounds of the part-formula (IC)

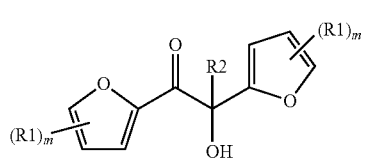

(IC)

in which R1, R2 and m have the meaning indicated above, and optionally (b) conversion of a base or acid of the compounds of the part-formula (IC) into one of their salts.

The compounds of the formula (I) and part-formula (IC) are particularly suitable for use in the lightening of skin, inhibition of tyrosinase, and/or prophylaxis, therapy and/or progress control of pigment disorders of the skin. These compounds can, in particular, also be combined with self-tanning substances which are based on the principle of the generation of coloured pigments by non-enzymatic tanning reaction of the self-tanning substances with keratin-containing matrices, so that a more uniform skin shade is achieved. Otherwise, the prior teaching of the invention and embodiments thereof relating to the use of compounds of the formula (I) and preparation thereof is valid and can be applied without restrictions to the compounds of the part-formula (IC) and the preparation and use thereof, if it appears appropriate.

Another embodiment of the present invention relates to a medicament comprising at least one compound of the formula (I) or part-formula (IC) and/or physiologically acceptable salts, tautomers, stereoisomers and/or solvates thereof, including mixtures thereof in all ratios. Still another embodiment of the invention is a pharmaceutical composition comprising, as active compound, an effective amount of at least one compound of the formula (IC) and/or physiologically acceptable salts, tautomers and/or stereoisomers thereof, including mixtures thereof in all ratios, together with pharmaceutically tolerated assistants. For both embodiments, a compound of the part-formula (IC) is preferred.

A "medicament", "drug" and a "pharmaceutical composition" or "pharmaceutical formulation" here is any composition which can be employed in the prophylaxis, therapy, progress control or aftertreatment of patients who, at least temporarily, exhibit a pathogenic modification of the overall condition or the condition of individual parts of the patient organism, preferably as a consequence of pigment disorders of the skin.

In order to increase the protective or therapeutic action of the compounds according to the invention, pharmaceutically tolerated adjuvants can be added. For the purposes of the invention, any substance which facilitates, enhances or modifies an effect with the compounds in accordance with the invention is an "adjuvant". Known adjuvants are, for example, aluminium compounds, such as, for example, aluminium hydroxide or aluminium phosphate, saponins, such as, for example, QS 21, muramyl dipeptide or muramyl tripeptide, proteins, such as, for example, gamma-interferon or TNF, MF 59, phosphatdibylcholine, squalene or polyols. Furthermore, DNA which encodes a protein with an adjuvant effect can be applied in parallel or in a construct.

The introduction of the pharmaceutical composition into a cell or organism can be carried out in accordance with the invention in any manner which enables tyrosinase to be brought into contact with the compounds present in the composition and as a consequence of which a response to be induced. The pharmaceutical composition of the present invention can be administered orally, topically, transdermally, transmucosally, transurethrally, vaginally, rectally, pulmonarily, enterally and/or parenterally, preferably topically or transdermally. The type of administration selected depends on the indication, the dose to be administered, individual-specific parameters, etc. In particular, the various types of administration facilitate site-specific therapy, which minimises side effects and reduces the active-compound dose.

The administration forms of the pharmaceutical composition are prepared corresponding to the desired type of administration in a suitable dosage and in a manner known per se using the customary solid or liquid vehicles and/or diluents and the assistants usually employed. Thus, pharmaceutically acceptable excipients known to the person skilled in the art can basically form part of the pharmaceutical composition according to the invention, where the amount of excipient material which is combined with the active compound in order to prepare a single dose varies depending on the individual to be treated and the type of administration. These pharmaceutically tolerated additives include salts, buffers, fillers, stabilisers, complexing agents, antioxidants, solvents, binders, lubricants, tablet coatings, flavours, dyes, preservatives, adjusters and the like. Examples of excipients of this type are water, vegetable oils, benzyl alcohols, alkylene glycol, polyethylene glycol, glycerol triacetate, gelatine, carbohydrates, such as, for example, lactose or starch, magnesium stearate, talc and Vaseline.

The pharmaceutical formulation can be in the form of a tablet, film tablet, dragee, lozenge, capsule, pill, powder, granules, syrup, juice, drops, solution, dispersion, suspension, suppository, emulsion, implant, cream, gel, ointment, paste, lotion, serum, oil, spray, aerosol, adhesive, plaster or bandage. Oral administration forms which are prepared are preferably tablets, film tablets, dragees, lozenges, capsules, pills, powders, granules, syrups, juices, drops, solutions, dispersions or suspensions—including as depot form. Furthermore, parenteral medicament forms, such as, for example, suppositories, suspensions, emulsions, implants or solutions, should be considered, preferably oily or aqueous solutions. For topical application, the medicament active compound is formulated in a conventional manner with at least one pharmaceutically acceptable vehicle, such as, for example, microcrystalline cellulose, and optionally further assistants, such as, for example, moisturisers, to give solid formulations which can be applied to the skin, such as, for example, creams, gels, ointments, pastes, powders or emulsions, or to give liquid formulations which can be applied to the skin, such as, for example, solutions, suspensions, lotions, sera, oils, sprays or aerosols. The pharmaceutical composition is preferably in a form for topical application. The pharmaceutical composition may also be in the form of a solid composition, for example in the lyophilised state, and can then be prepared before use by addition of a dissolving agent, such as, for example, distilled water. The person skilled in the art is familiar with the basic principles of the preparation of lyophilisates.

The concentration of the active compound in the formulation can be 0.01 to 100 percent by weight. It is crucial that the pharmaceutical composition comprises, as active compound, an effective amount of the compound together with the pharmaceutically tolerated assistants. The terms "effective amount" or "effective dose" are used interchangeably herein and denote an amount of the pharmaceutical active compound which has a prophylactically or therapeutically relevant effect on a disease or pathological change in cell, tissue, organ or mammal. A "prophylactic effect" prevents the outbreak of a disease and also includes an increase in normal physiological function. Prophylaxis is advisable, in particular, if an individual has predispositions for the onset of the above-mentioned diseases, such as, for example, a family history, a gene defect or a recently survived disease. A "therapeutically relevant effect" results in part or full freedom from one, more than one or all disease symptoms or results in the partial or complete return of one, more than one or all physiological or biochemical parameters which are associated with or causally involved in the disease or pathological change to the normal state. Progress control is also taken to be a type of therapeutic treatment if the compounds are administered at certain intervals, for example in order completely to eliminate the symptoms of a disease. The respective dose or dose range for the administration of the compounds according to the invention is sufficiently large to achieve the desired prophylactic or therapeutic effect of induction of a biological or medical response. In general, the dose will vary with the age, constitution and gender of the patient, and the severity of the disease will be taken into account. It goes without saying that the specific dose, frequency and duration of administration are, in addition, dependent on a multiplicity of factors, such as, for example, the targeting and bonding ability of the compounds, feeding habits of the individual to be treated, type of administration, excretion rate and combination with other drugs. The individual dose can be adjusted both with respect to the primary disease and also with respect to the occurrence of any complications. The precise dose can be established by a person skilled in the art using known means and methods.

In an embodiment of the invention, the compounds are administered in a dose of 0.01 mg to 1 g per dosage unit, preferably between 1 to 700 mg, particularly preferably 5 to 100 mg. The daily dose is in particular between 0.02 and 100 mg/kg of body weight.

In order to support the medical effect, the pharmaceutical composition may, in an embodiment of the invention, also comprise one or more further active compounds, where simultaneous or successive administration is conceivable. The therapeutic effect of the pharmaceutical composition according to the invention can consist, for example, in certain skin lighteners having a better action through the inhibition of tyrosinase as a desired side effect or in the number of side effects of these drugs being reduced by the reduction in the dose. The prior teaching of the invention and embodiments thereof relating to the combination of compounds of the formula (I) with further active compounds and preparations of this type is valid and can be applied without restrictions to combination preparations with the compounds of the part-formula (IC) and preparations thereof, if it appears appropriate.

The invention can also be practised as a kit which comprises the compounds according to the invention. The kit consists of separate packs of (a) an effective amount of a compound of the part-formula (IC) and/or physiologically acceptable salts, tautomers and/or stereoisomers thereof, including mixtures thereof in all ratios, and (b) an effective amount of a further active compound. The kit comprises suitable containers, such as, for example, boxes or cartons, individual bottles, bags or ampoules. The kit may, for example, comprise separate ampoules, each containing an effective amount of a compound of the part-formula (IC) and/or pharmaceutically usable salts, tautomers and/or stereoisomers thereof, including mixtures thereof in all ratios, and an effective amount of a further medicament active compound in dissolved or lyophilised form. The kit of the invention may also contain an article which contains written instructions or points the user towards written instructions which explain the handling of the compounds of the invention.

The invention furthermore teaches a method for the prophylaxis, therapy and/or progress control of pigment disorders of the skin in which an effective amount of at least one compound of the formula (I), part-formula (IA), (IB), (IC) and/or physiologically acceptable salts, tautomers and/or stereoisomers thereof, including mixtures thereof in all ratios, is administered to a subject to be treated. Preferred subjects in the sense of the invention are humans or animals, particularly preferably humans. It is known to the person skilled in the art here that he can administer the above-mentioned compounds of the invention, which can of course also be used as the pharmaceutical composition, in various doses to an organism, in particular a human patient. The effective amount and the type of administration can be determined by the person skilled in the art by routine experiments. The prior teaching of the invention and embodiments thereof are valid and can be applied without restrictions to the treatment method, if it appears appropriate.

As part of the invention presented here, novel 2,2'-furoin derivatives of the formula (I) were provided for the first time. The compounds according to the invention target tyrosinase affinitively and/or selectively. The compounds of the formula (I), part-formulae thereof and derivatives thereof are distinguished by high specificity and stability, low preparation costs and easy handling. These properties form the basis for a reproducible mode of action, including the absence of cross-reactivities, and reliable and safe interaction with the corresponding target structures. The invention also includes the use of the present 2,2'-furoin derivatives of the formula (I) for the inhibition, regulation and/or modulation of the signalling cascade of tyrosinase and thus offers novel tools for research and/or diagnostics.

Pharmaceutical compositions which comprise the said compounds and the use of these compounds for the treatment of tyrosinase-promoted disorders are a highly promising approach for achieving direct and immediate alleviation of symptoms in humans and animals. This is particularly advantageous for effective treatment of pigment disorders, either as monotherapy or in combination with other skin-lightening therapies. The control of skin pigmentation is likewise a central topic of modern cosmetic products. Whether a very pale or rather a tanned appearance is preferred is crucially dependent on cultural factors. Products which serve for skin lightening are, for example, of particular interest in the Asian culture area, where a pale skin shade is associated with a raised social position and financial wealth.

Owing to the strong and selective inhibition of tyrosinase, which regulates the skin shade via the synthesis of melanin, the compounds of the formula (I) can, in accordance with the invention, be administered in considerably lower concentration, while they achieve similar or even superior biological efficacy compared with the less-potent skin-lightening substances of the prior art. They advantageously exhibit a high and long-lasting activity with respect to their action as skin-lightening active compounds. The application is also accompanied by reduced or no medical side effects, in particular as no skin irritation occurs. The active compounds according to the invention are distinguished not only by improved efficacy, but also by use safety and good formulation ability. Thus, they can easily be incorporated into preparations and have increased stability in the preparations.

Even without further comments, it will be assumed that a person skilled in the art will be able to utilise the above description in the broadest scope. All said and further constituents or components are familiar to the person skilled in the art and can experience a specific embodiment for the teaching according to the invention in routine experiments. All documents cited in the description are hereby intended to be incorporated in their entirety into the disclosure content of the present invention as reference.

The preferred embodiments and examples should merely be regarded as descriptive disclosure which is absolutely not limiting in any way. It consequently goes without saying that this invention is not restricted to the specific compounds, pharmaceutical compositions, uses, methods and processes as described herein, since such things can vary. It furthermore goes without saying that the terminology used herein serves exclusively the purpose of the description of particular embodiments and is not intended to restrict the scope of protection of the invention. As used herein in the specification, including the appended claims, word forms in the singular, such as, for example, "a" or "the", include the equivalent in the plural, so long as the context does not specifically indicate otherwise. For example, the reference to "a compound" includes a single compound or a plurality of compounds, which may in turn be identical or different, or the reference to "a process" includes equivalent steps and processes which are known to the person skilled in the art.

The invention is explained in greater detail below with reference to non-limiting examples of specific embodiments. The examples should, in particular, be interpreted as not being restricted to the feature combinations specifically illustrated, but instead the illustrative features can in turn be freely combined or used individually so long as the object of the invention is achieved. The percent by weight ratios of the individual ingredients in the preparations of the examples expressly belong to the disclosure content of the description and can therefore be used as features.

EXAMPLE 1

Synthesis of 2,2'-furoin

The synthesis of compounds according to the invention is possible from correspondingly unsubstituted or substituted furfural derivatives by means of benzoin condensation. This reaction has been widely described in the chemical literature. In the specific case, the synthesis can be carried out, for example, as described in DE-A-19704273:

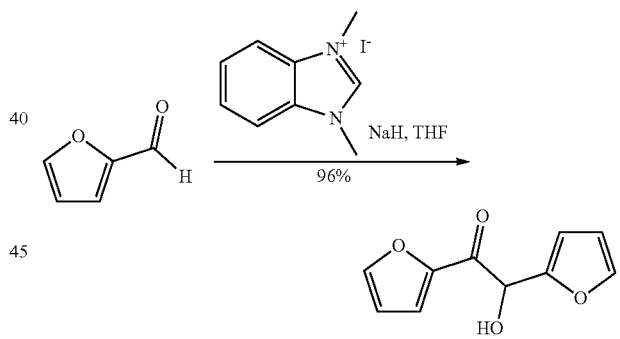

EXAMPLE 2

Tyrosinase Assay

The action of the compounds having the formula (I) as skin lighteners is tested through their ability to inhibit the enzyme tyrosinase and thus to suppress melanin synthesis. The inhibiting action of the compounds of the formula (I) or part-formulae thereof against tyrosinase is assessed using tyrosinase from fungi and L-DOPA as substrate. The compounds and L-dopa are pre-incubated at 25° C. for 10 minutes in phosphate buffer (pH 6.8), and tyrosinase from fungi (16 U) (Fluka) is subsequently added. The optical density of the samples is measured at 470 nm against a negative control (without active compound). Kojic acid is likewise tested as tyrosinase reference, i.e. positive control.

EXAMPLE 3

B16 V Mouse Melanoma Cell Tests

B16V mouse melanoma cells (manufacturer: DSMZ; Article No.: ACC370) are transferred into RPMI medium (Invitrogen, Article No.: 31870), to which 10% of FBS (foetal bovine serum; Invitrogen, Article No.: 10499044), 2 mM L-glutamine (Invitrogen, Article No: 25030) and 1 mM sodium pyruvate (Invitrogen, Article No.: 11360) had additionally been added, and incubated at 37° C. and 5% $CO_2$ for 72 h. The medium is separated off, and the cells are washed once with 10 ml of DPBS (Dulbecco's phosphate-buffered salines; Invitrogen, Article No.: 14190), and the medium is subsequently removed by suction. 1 ml of HyQtase cell detachment solution (Hyclone, Article No.: SV30030.01) is added to the cells. The bottle is swirled a number of times, and the HyQtase cell detachment solution is subsequently removed by suction. The cells are then incubated in the incubator at 37° C. and 5% $CO_2$ for 5 min. The cells are taken up in the modified RPMI medium (see above), and the cell count is determined. To this end, the cells are stained with Trypan Blue and counted in a Neubauer counting chamber. The cells are subsequently sown out again in the modified RPMI medium (see above) in a defined cell count of 80,000 cells per well (6-well clear plate, TCT, PS (Nunc)).

The cells are incubated at 37° C. and 5% $CO_2$ for 24 h, the medium is then removed. 1980 µl of the substance dilution are subsequently added. For this substance dilution, 2,2'-furoin is dissolved in DMSO and subsequently filtered through a sterile filter (0.2 µm, Millipore, Article No. SLLG013SL). The solution is then diluted with the modified RPMI medium (see above, but in this case the FBS content is only 5%) in such a way that the final concentration of the 2,2'-furoin dilution is 0.1 mM or 0.05 mM. 20 µl of an alpha-MSH solution (alpha-melanocyte-stimulating hormone, DMSO, Sigma, Article No.: D2650) are then added, so that the alpha-MSH concentration in the well is $10^{-8}$ M. The plate is subsequently incubated again at 37° C. and 5% $CO_2$ for 24 h. The process described in this section is repeated a further twice in total.

After the final incubation period, the medium is removed by suction, and the cells are washed with 1000 µl of DPBS (Invitrogen, Article No.: 14190). The medium is again removed by suction. 250 µl of HyQtase cell detachment solution (Hyclone, Article No.: SV30030.01) are added to the cells. The 6-well plate is swirled a number of times, and the HyQtase cell detachment solution is subsequently removed by suction. The cells are then incubated in the incubator at 37° C. and 5% $CO_2$ for 5 min. The cells are taken up in 1.5 ml of DPBS (Invitrogen, Article No.: 14190) and transferred into a cup (SARSTEDT, Ref. 72.692.005). The cell count is subsequently determined. To this end, the cells are stained with Trypan Blue and counted in a Neubauer counting chamber. The cells centrifuged for 1 min at 3500 g. The pellets obtained are photographed, and the supernatant is subsequently removed by suction. The pellets are dissolved in 1 ml of 1 N NaOH at 80° C. for 1 h and then cooled to RT. Four times 200 µl per cup (as quadruple determination) are subsequently pipetted into a 96-well plate (VWR, Article No.: 4100636981), and the absorption at a wavelength of 405 nm is determined (Safire, Tecan). The content of melanin can be determined in this way by means of a calibration line.

TABLE 1

Skin-lightening effect of various active compounds in comparison.

| Active compound | Relative melanin content in % |
|---|---|
| DMSO (solvent-blank value) | 100 |
| DMSO + alpha-MSH | 235 |
| Kojic acid (1 mM) + alpha-MSH | 96 |
| 2,2'-Furoin (0.1 mM) + alpha-MSH | 63.1 |
| 2,2'-Furoin (0.05 mM) + alpha-MSH | 88.0 |

A significant improvement can be demonstrated compared with skin-lightening substances known in the prior art, since an effect is achieved with considerably lower concentrations (Table 1).

EXAMPLE 4

Melanogenesis Assay with Human Primary Cells

An ampoule of normal human epidermal melanocytes (NHEM, Promocell) is thawed and divided into further bottles depending on the number of their duplicates. After 2 to 3 weeks, between 750,000 and one million cells are transferred into T25 bottles with 5 ml of full medium. After 24 hours, the medium is removed and replaced by corresponding substance dilutions or controls. The overall duration of the incubation of the various test substances on the cells is 10 days. During these 10 days, the substance dilutions or controls are replaced every 2-3 days. After 10 days, the melanocytes are harvested. 500 µl of trypsin/EDTA is added to the cells and immediately removed again by suction. The cells are subsequently taken up in medium, counted and centrifuged off. The supernatant is removed, the pellet is washed with DPBS and centrifuged again. A photo of this pellet is taken. The pellet is then taken up in 1 ml of NaOH (1 M) and incubated in a shaker at 80° C. for one hour. The solution, cooled to room temperature, is pipetted into a 96-well plate (4×200 µl), and the absorption at 405 nm is measured. The values measured are subsequently plotted in percent against the control.

TABLE 2

Skin-lightening effect of various active compounds in comparison.

| Active compound | Relative melanin content in % |
|---|---|
| DMSO | 100 |
| 2,2'-Furoin | 72.9 |

A significant improvement can be demonstrated compared with skin-lightening substances known in the prior art, since an effect is achieved with considerably lower concentrations (Table 2).

EXAMPLE 5

Preparations

Recipes for cosmetic preparations which comprise compound according to Example 1 are indicated below by way of example (Tables 3-5). In addition, the INCI names of the commercially available compounds are indicated. UV-Pearl, OMC stands for the preparation with the INCI name: Water (for EU: Aqua), Ethylhexyl Methoxycinnamate, Silica, PVP, Chlorphenesin, BHT; this preparation is commercially available under the name Eusolex® UV Pearl™ OMC from Merck KGaA, Darmstadt. The other UV-Pearl indicated in the tables each have an analogous composition, with OMC having been replaced by the UV filters indicated.

TABLE 3

W/O emulsions (figures in % by weight).

|  | 1-1 | 1-2 | 1-3 | 1-4 | 1-5 | 1-6 | 1-7 | 1-8 | 1-9 |
|---|---|---|---|---|---|---|---|---|---|
| Titanium dioxide |  | 2 | 5 |  |  |  |  |  |  |
| 2,2'-Furoin | 0.1 | 0.01 | 0.001 | 0.2 | 0.25 | 0.3 | 0.4 | 0.5 | 1.0 |
| Zinc oxide |  |  |  |  |  |  |  | 5 | 2 |
| UV-Pearl, OMC | 30 | 15 | 15 | 15 | 15 | 15 | 15 | 15 | 15 |
| Polyglyceryl-3-Dimerate | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 |
| Hexyl Laurate | 4 | 4 | 4 | 4 | 4 | 4 | 4 | 4 | 4 |
| PVP/Eicosene Copolymer | 2 | 2 | 2 | 2 | 2 | 2 | 2 | 2 | 2 |
| Propylene Glycol | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 |

|  | 1-11 | 1-12 | 1-13 | 1-14 | 1-15 | 1-16 | 1-17 | 1-18 |
|---|---|---|---|---|---|---|---|---|
| Titanium dioxide | 3 |  | 2 |  | 3 |  | 2 | 5 |
| Benzylidene malonate polysiloxane |  | 1 | 0.5 |  |  |  |  |  |
| Methylene Bis-Benztriazolyl Tetramethylbutylphenol | 1 | 1 | 0.5 |  |  |  |  |  |
| 2,2'-Furoin | 0.1 | 0.01 | 0.001 | 0.2 | 0.25 | 0.5 | 1.0 | 2.0 |
| Polyglyceryl-3-Dimerate | 3 | 3 | 3 | 3 |  |  |  |  |
| Cera Alba | 0.3 | 0.3 | 0.3 | 0.3 | 2 | 2 | 2 | 2 |
| Hydrogenated Castor Oil | 0.2 | 0.2 | 0.2 | 0.2 |  |  |  |  |
| Paraffinium Liquidum | 7 | 7 | 7 | 7 |  |  |  |  |
| Caprylic/Capric Triglyceride | 7 | 7 | 7 | 7 |  |  |  |  |
| Hexyl Laurate | 4 | 4 | 4 | 4 |  |  |  |  |
| PVP/Eicosene Copolymer | 2 | 2 | 2 | 2 |  |  |  |  |
| Propylene Glycol | 4 | 4 | 4 | 4 |  |  |  |  |
| Magnesium Sulfate | 0.6 | 0.6 | 0.6 | 0.6 |  |  |  |  |
| Tocopherol | 0.5 | 0.5 | 0.5 | 0.5 |  |  |  |  |
| Tocopheryl Acetate | 0.5 | 0.5 | 0.5 | 0.5 | 1 | 1 | 1 | 1 |
| Cyclomethicone | 0.5 | 0.5 | 0.5 | 0.5 |  |  |  |  |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate |  |  |  |  | 6 | 6 | 6 | 6 |
| PEG-7 Hydrogenated Castor Oil |  |  |  |  | 1 | 1 | 1 | 1 |
| Zinc Stearate |  |  |  |  | 2 | 2 | 2 | 2 |
| Oleyl Erucate |  |  |  |  | 6 | 6 | 6 | 6 |
| Decyl Oleate |  |  |  |  | 6 | 6 | 6 | 6 |
| Dimethicone |  |  |  |  | 5 | 5 | 5 | 5 |
| Trometamine |  |  |  |  | 1 | 1 | 1 | 1 |
| Glycerin |  |  |  |  | 5 | 5 | 5 | 5 |
| Allantoin |  |  |  |  | 0.2 | 0.2 | 0.2 | 0.2 |
| Water | to 100 | to 100 | to 100 | to 100 | to 100 | to 100 | to 100 | to 100 |

TABLE 4

O/W emulsions (figures in % by weight).

|  | 2-1 | 2-2 | 2-3 | 2-4 | 2-5 | 2-6 | 2-7 | 2-8 | 2-9 | 2-10 |
|---|---|---|---|---|---|---|---|---|---|---|
| Titanium dioxide |  | 2 | 5 |  |  |  |  |  |  | 3 |
| Methylene Bis-Benztriazolyl Tetramethylbutylphenol |  |  |  |  |  | 1 | 2 | 1 |  |  |
| 2,2'-Furoin | 0.1 | 0.01 | 0.001 | 0.25 | 0.6 | 0.5 | 0.3 | 0.5 | 0.5 | 0.6 |
| 4-Methylbenzylidene Camphor | 2 |  | 3 |  | 4 |  | 3 |  | 2 |  |
| BMDBM | 1 | 3 |  | 3 | 3 |  | 3 | 3 | 3 |  |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |

TABLE 4-continued

O/W emulsions (figures in % by weight).

| | | | | | | | | | | |
|---|---|---|---|---|---|---|---|---|---|---|
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| *Persea Gratissima* | | | | | | | | | | |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | | 1.8 | | | | | | |
| Glycerin | | | | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium dioxide | 3 | | 2 | | | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| 2,2'-Furoin | 5 | 5 | 5 | 5 | 5 | 5 | 5 | 5 |
| Zinc oxide | | | 2 | | | | | |
| UV-Pearl, OMC | 15 | 15 | 15 | 30 | 30 | 30 | 15 | 15 |
| 4-Methylbenzyliden Camphor | | | | 3 | | | | |
| BMDBM | | | | 1 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| *Persea Gratissima* | | | | | 8 | 8 | 8 | 8 |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Tromethamine | | | | | 1.8 | | | |
| Glycerin | | | | | 3 | 3 | 3 | 3 |
| Water | to 100 | to 100 | to 100 | to 100 | to 100 | to 100 | to 100 | to 100 |

TABLE 5

Gels (figures in % by weight).

| | 3-1 | 3-2 | 3-3 | 3-4 | 3-5 | 3-6 | 3-7 | 3-8 | 3-9 | 3-10 |
|---|---|---|---|---|---|---|---|---|---|---|
| Titanium dioxide | | 2 | 5 | | | | | | | 3 |
| 2,2'-Furoin | 0.4 | 0.5 | 0.01 | 0.7 | 0.4 | 0.3 | 0.001 | 0.7 | 0.6 | 0.7 |
| Benzylidene malonate polysiloxane | | | 1 | 1 | 2 | | | | 1 | 1 |
| Methylene Bis-Benztriazolyl Tetramethylbutylphenol | | 1 | | | | 1 | 2 | 1 | | |
| Zinc oxide | | | | 2 | | | | 5 | 2 | |
| UV-Pearl, Ethylhexyl Mehtoxycinnamat | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| *Prunus Dulcis* | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |

TABLE 5-continued

| Gels (figures in % by weight). | | | | | | | | | | |
|---|---|---|---|---|---|---|---|---|---|---|
| | 3-1 | 3-2 | 3-3 | 3-4 | 3-5 | 3-6 | 3-7 | 3-8 | 3-9 | 3-10 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

The invention claimed is:

1. A method for lightening the skin; for inhibiting tyrosinase; or for the therapy of a tyrosinase-promoted disorder of the skin, comprising administering to a subject in need thereof an effective amount of a compound of formula (I)

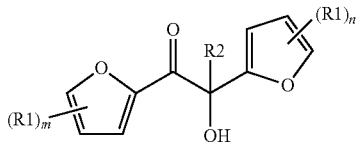

(I)

in which
R1 denotes A, Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar,
R2 denotes H, A, Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar,
Y denotes H or Alk,
A denotes unbranched or branched alkyl having 1-18 C atoms, where, independently of one another, 1-3 H atoms are optionally replaced by F and/or, independently of one another, one or two adjacent CH$_2$ groups are optionally replaced by —O—, —N(Alk)-, a —CH=CH— and/or —C≡C— group,
Alk denotes unbranched or branched alkyl having 1-12 C atoms,
Cyc denotes cyclic alkyl having 3-10 C atoms, where, independently of one another, 1-3 H atoms are optionally replaced by F and/or, independently of one another, one or two adjacent CH$_2$ groups are optionally replaced by —O—, —N(Alk)-, a —CH=CH— and/or —C≡C— group,
Ar denotes a mono-, bi- or tricyclic aromatic carbocycle having 3 to 20 C atoms, which is unsubstituted or mono-, di- or trisubstituted by F, A, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY, and
m, n, p, independently of one another, denote 0, 1, 2 or 3, or a pharmaceutically acceptable salt, tautomer, stereoisomer or solvate thereof.

2. A method according to claim 1, which is for the inhibition of tyrosinase.

3. A method according to claim 1, which is for the therapy of a tyrosinase-promoted disorder of the skin.

4. A method according to claim 3, where the tyrosinase-promoted disorder of the skin is hyperpigmentation, freckles, age spots or sun spots.

5. A method according to claim 1, wherein the compound of formula (I) is of formula (IA)

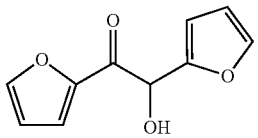

(IA)

or (IB)

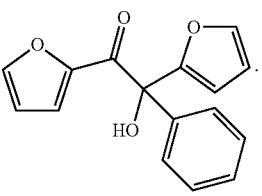

(IB)

6. A method according to claim 1, which is for lightening the skin.

7. A method according to claim 1, which is for the therapy and/or progress control of a pigment disorder of the skin.

8. A method according to claim 1, wherein the compound of formula (I) is of formula (IA)

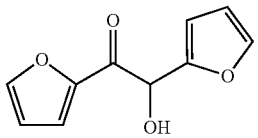

(IA)

9. A composition, comprising at least one compound of the formula (I)

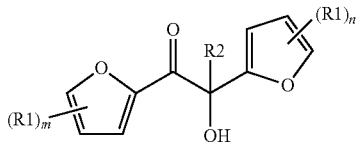

(I)

in which
R1 denotes A, Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar, R2 denotes H, A, Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar, Y denotes H or Alk, A denotes unbranched or branched alkyl having 1-18 C atoms, where, independently of one another, 1-3 H atoms are optionally replaced by F and/or, independently of one another, one or two adjacent CH$_2$ groups are optionally replaced by —O—, —N(Alk)-, a —CH═CH— and/or —C≡C— group, Alk denotes unbranched or branched alkyl having 1-12 C atoms, Cyc denotes cyclic alkyl having 3-10 C atoms, where, independently of one another, 1-3 H atoms are optionally replaced by F and/or, independently of one another, one or two adjacent CH$_2$ groups are optionally replaced by —O—, —N(Alk)-, a —CH═CH— and/or —C≡C— group, Ar denotes a mono-, bi- or tricyclic aromatic carbocycle having 3 to 20 C atoms, which is unsubstituted or mono-, di- or trisubstituted by F, A, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY, and m, n, p, independently of one another, denote 0, 1, 2 or 3, or a pharmaceutically acceptable salt, tautomer, stereoisomer or solvate thereof and at least one further active compound selected from the group consisting of antioxidants, vitamins, UV filters, skin-lightening active compounds, self-tanning substances, antimicrobial active compounds, skin-moisture regulators, antiinflammatory active compounds, anti-ageing active compounds, anticellulite active compounds, anti-wrinkle active compounds and antidandruff active compounds.

10. A composition according to claim 9, further comprising one or more antioxidants, one or more vitamins and/or one or more UV filters.

11. A composition according to claim 9, further comprising one or more self-tanning substances.

12. A composition according to claim 9, further comprising at least one further active compound or extract having a skin-lightening activity.

13. A composition according to claim 9, further comprising a vehicle which is suitable for cosmetic, pharmaceutical or dermatological applications and optionally physiologically acceptable assistants and/or fillers.

14. A composition according to claim 9, further comprising DHA, DHA plus, DHA rapid or erythrulose.

15. A composition according to claim 9, further comprising hydroquinone, niacinamide, ascorbic acid, a physiologically acceptable salt of ascorbic acid, kojic acid, arbutin, aloesin, azelaic acid, elagic acid, rucinol, liquorice extract, mulberry extract or emblica.

16. A composition according to claim 9, wherein in the compound of formula (I)

R2 denotes A, Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar.

17. A composition according to claim 9, wherein in the compound of formula (I)

R2 denotes Cyc, F, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or Ar.

18. A process for preparing a composition according to claim 9, comprising mixing together at least one compound of the formula (I) or a pharmaceutically acceptable salt, tautomer, stereoisomer or solvate thereof with at least one further active compound and at least one vehicle which is suitable for topical applications and optionally with physiologically acceptable assistants and/or fillers.

19. A compound of formula (I)

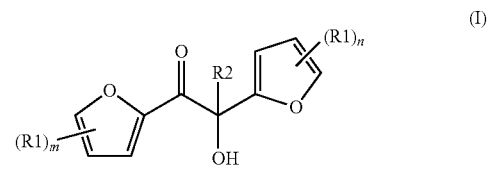

in which

R1 denotes A, Cyc, OH or Ar,

R2 denotes Y, Cyc, OH or Ar,

Y denotes H or Alk,

A denotes unbranched or branched alkyl having 5-18 C atoms, where, independently of one another, 1-3 H atoms are optionally replaced by F and/or, independently of one another, one or two adjacent CH$_2$ groups are optionally replaced by —O—, —N(Alk)-, a —CH═CH— or —C≡C— group, Alk denotes unbranched or branched alkyl having 1-12 C atoms, Cyc denotes cyclic alkyl having 3-8 C atoms, where, independently of one another, 1-3 H atoms are optionally replaced by F and/or, independently of one another, one or two adjacent CH$_2$ groups are optionally replaced by —O—, —N(Alk)- or a —CH═CH— group, Ar denotes mono-, bi- or tricyclic aryl having 5 to 14 C atoms, which is unsubstituted or mono-, di- or trisubstituted by F, Alk or —(CY$_2$)$_p$—OY, and m, p, independently of one another, denote 0, 1 or 2, with the proviso that Y and Ar are excluded for R2 if m and n simultaneously denote 0, or a pharmaceutically acceptable salt, tautomer, stereoisomer or solvate thereof.

20. A compound according to claim 19, wherein R2 denotes Cyc.

21. A process for preparing a compound of formula (IC)

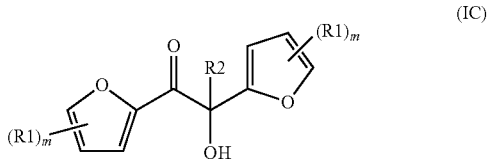

in which

R1 denotes A, Cyc, OH or Ar,

R2 denotes Y, Cyc, OH or Ar,

Y denotes H or Alk,

A denotes unbranched or branched alkyl having 5-8 C atoms, where, independently of one another, 1-3 H atoms are optionally replaced by F and/or, independently of one another, one or two adjacent CH$_2$ groups are optionally replaced by —O—, —N(Alk)-, a —CH═CH— or —C≡C— group, Alk denotes unbranched or branched alkyl having 1-4 C atoms, Cyc denotes cyclic alkyl having 3-8 C atoms, where, independently of one another, 1-3 H atoms are optionally replaced by F and/or, independently of one another, one or two adjacent CH$_2$ groups are optionally replaced by —O—, —N(Alk)- or a —CH=CH— group, Ar denotes mono-, bi- or tricyclic aryl having 5 to 14 C atoms, which is unsubstituted or mono-, di- or trisubstituted by F, Alk or —(CY$_2$)$_p$—OY, and m, p, independently of one another, denote 0, 1 or 2, with the proviso that Y and Ar are excluded for R2 if m denotes 0, or a pharmaceutically acceptable salt, tautomer, stereoisomer or solvate thereof comprising (a) benzoin addition of a furfural compound of formula (II)

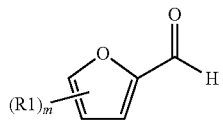
(II)

in which R1 and m have the meaning indicated above, to give a compound of formula (IC)

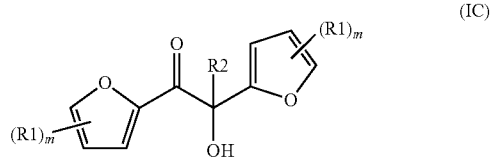
(IC)

in which R1, R2 and m have the meaning indicated above, and optionally (b) converting a base or acid compound of formula (IC) into a salt.

22. A pharmaceutical composition, comprising at least one compound of formula (I) according to claim 19 or a pharmaceutically acceptable salt, tautomer, stereoisomer or solvate thereof, and a pharmaceutically acceptable carrier.

* * * * *